(12) United States Patent
Reiner et al.

(10) Patent No.: US 10,180,441 B2
(45) Date of Patent: Jan. 15, 2019

(54) MICROPLATE-READER WITH A CONTROLLED GAS ATMOSPHERE AND A CORRESPONDING METHOD OF CONTROLLING THE GAS ATMOSPHERE

(71) Applicant: TECAN Trading AG, Männedorf (CH)

(72) Inventors: Florian Reiner, Anger (DE); Harald Gebethsroither, Grödig Österreich (AT); Josef Grassl, Schönau am Königsee (DE)

(73) Assignee: TECAN TRADING AG, Mannedorf (CH)

( * ) Notice: Subject to any disclaimer, the term of this patent is extended or adjusted under 35 U.S.C. 154(b) by 0 days.

(21) Appl. No.: 14/870,673

(22) Filed: Sep. 30, 2015

(65) Prior Publication Data

US 2016/0018429 A1    Jan. 21, 2016

Related U.S. Application Data

(63) Continuation-in-part of application No. 13/227,761, filed on Sep. 8, 2011, now Pat. No. 9,322,784.

(Continued)

(51) Int. Cl.

| | |
|---|---|
| *C12M 1/00* | (2006.01) |
| *G01N 35/02* | (2006.01) |
| *C12M 1/04* | (2006.01) |
| *G01N 33/50* | (2006.01) |
| *G01N 21/64* | (2006.01) |

(Continued)

(52) U.S. Cl.
CPC ............. *G01N 35/028* (2013.01); *C12M 1/04* (2013.01); *C12M 41/14* (2013.01); *C12M 41/16* (2013.01); *C12Q 1/02* (2013.01); *G01N 21/253* (2013.01); *G01N 21/6452* (2013.01); *G01N 33/5005* (2013.01); *B01L 9/52* (2013.01); *G01J 3/12* (2013.01); *G01N 2035/00356* (2013.01); *G01N 2201/023* (2013.01); *G01N 2201/0231* (2013.01); *G01N 2201/0238* (2013.01);

(Continued)

(58) Field of Classification Search
None
See application file for complete search history.

(56) References Cited

U.S. PATENT DOCUMENTS 3,618,734 A * 11/1971 Khan ................... C12M 23/48
119/318
4,936,682 A * 6/1990 Hoyt ..................... G01N 21/253
250/576

(Continued)

*Primary Examiner* — Neil N Turk
(74) *Attorney, Agent, or Firm* — Notaro, Michalos & Zaccaria P.C.

(57) ABSTRACT

The invention relates to a microplate reader and a respective method, wherein the microplate reader comprises at least one measuring device and a holding device for accommodating at least one microplate and for positioning the samples-containing wells of this(these) microplate(s) in relation to the at least one measuring device. The at least one measuring device is used for detecting light which is emitted by samples in wells of a microplate inserted in this microplate reader and/or which is influenced by samples transilluminated by light in wells of a microplate inserted in this microplate reader. The microplate reader comprises a control unit for controlling the temperature of a gas atmosphere surrounding the wells containing the samples of microplates used in this microplate reader.

16 Claims, 5 Drawing Sheets

Related U.S. Application Data

(60) Provisional application No. 61/380,783, filed on Sep. 8, 2010.

(51) Int. Cl.
  *C12M 1/34* (2006.01)
  *G01N 21/25* (2006.01)
  *C12Q 1/02* (2006.01)
  *B01L 9/00* (2006.01)
  *G01J 3/12* (2006.01)
  *G01N 35/00* (2006.01)

(52) U.S. Cl.
  CPC ............... *G01N 2201/0446* (2013.01); *G01N 2201/06113* (2013.01)

(56) References Cited

U.S. PATENT DOCUMENTS

| | | | | |
|---|---|---|---|---|
| 5,681,492 | A * | 10/1997 | Van Praet | B01L 7/02 219/386 |
| 6,719,449 | B1 * | 4/2004 | Laugharn, Jr. | B01F 11/02 366/127 |
| 2005/0191756 | A1 * | 9/2005 | Corson | G01N 21/15 436/164 |
| 2008/0191149 | A1 * | 8/2008 | Zimenkov | G01J 3/10 250/492.1 |
| 2010/0260422 | A1 * | 10/2010 | Ito | C12M 41/14 382/190 |

* cited by examiner

MICROPLATE-READER WITH A CONTROLLED GAS ATMOSPHERE AND A CORRESPONDING METHOD OF CONTROLLING THE GAS ATMOSPHERE

RELATED APPLICATIONS

This patent application is a continuation-in-part application of the U.S. patent application Ser. No. 13/227,761, which is published as US 2012/0064564 A1 and which claims priority of the U.S. provisional application No. 61/380,783 of Sep. 8, 2010, the disclosure of both applications is incorporated herein by reference in its entirety for any purpose.

TECHNICAL FIELD OF THE INVENTION

The invention relates to a microplate reader which comprises at least one measuring device, one holding device, and a control unit. The at least one measuring device is used for the detection of light which is emitted by samples in wells of a microplate inserted in said microplate reader and/or which is influenced by samples penetrated by light in wells of a microplate inserted in said microplate reader. The holding device is used for accommodating at least one microplate and for positioning the wells of said microplate(s) containing the samples in relation to the at least one measuring device. The control unit is used for controlling a gas atmosphere surrounding wells of a microplate inserted in said microplate reader. The invention further relates to a method of controlling said gas atmosphere.

RELATED PRIOR ART

Generic microplate readers which have been known for many years in the state of the art are based on the principle of the measurement of luminescence and/or fluorescence of samples treated with a reagent. Luminescence or fluorescence generally refers to the emission of light which originates from a sample, wherein the luminescence is caused by the progression of a chemical reaction in a sample and the fluorescence is caused by the irradiation of an excitation light. Such microplate readers are used for observing reactions in samples to which a reagent is added or for detecting specific sample components which can be made to fluoresce. Respective microplate readers are known which—for the purpose of triggering a luminescent reaction—comprise an injector apparatus for adding a reagent to the samples in wells of the microplate(s) used in respectively inserted into this microplate reader. Microplate readers are also known which comprise an illumination device for irradiating or transilluminating samples in wells of the microplate(s) used in this microplate reader. Such microplate readers are used to measure the fluorescence excited in the samples or the reduction in the transparency (the absorbance) caused by the samples.

OBJECTS AND SUMMARY OF THE INVENTION

It is an object of the present invention to propose a microplate reader, respective methods for measuring living cells in a microplate reader and uses of such a microplate reader which enable the observation of reactions in samples and/or the detection of specific sample components under at least approximately physiological conditions.

This object is achieved with respect to a first aspect by a microplate reader as herein disclosed. This microplate reader comprises:
a) at least one measuring device, which is selected from a group comprising:
   a1) a first measurement device which is designed for measuring the absorbance of samples in wells of a microplate used or inserted in the microplate-reader,
   a2) a second measurement device which is designed for measuring the fluorescence of samples that are irradiated with light in wells of a microplate used or inserted in the microplate-reader, and
   a3) a third measurement device which is designed for measuring the luminescence of samples in wells of a microplate used or inserted in the microplate-reader;
b) a holding device for accommodating at least one microplate and for positioning the samples-containing wells of these microplate(s) in relation to at least one measuring device;
c) a control unit for controlling the composition of the gas atmosphere surrounding the samples-containing wells of microplates used or inserted in this microplate reader.

The microplate-reader further comprises alternatively:
d1) a separating plate which subdivides an interior space of a housing of the microplate-reader into an appliance compartment and a sample compartment and which comprises at least one opening, which separating plate is designed such that light which is irradiated or influenced by samples in wells of a microplate used in the microplate-reader can pass therethrough from the samples compartment to the appliance compartment, or
d2) an interior housing, which is arranged within a housing of the microplate-reader, within which the holding device is arranged, which interior housing subdivides an interior space of the housing of the microplate-reader into an appliance compartment and a sample compartment surrounding the holding device, and which comprises at least one opening, which is designed such that light which is irradiated or influenced by samples in wells of a microplate used in the microplate-reader can pass therethrough from the samples compartment to the appliance compartment.

A main function of the separating plate and of the interior housing is common to these two alternative zoning means, i.e. separating of the sample compartment from the appliance compartment in a way that the samples in the sample compartment are influenced by the appliances only as desired.

In the interior space of the housing, the microplate-reader can be designed such that the sample compartment is separated from the appliance compartment substantially light-tight and substantially gas-tight by means of the separating plate respectively the interior housing. To this end, the opening may comprise an according proofing device. Alternatively or in addition, a proofing device which extends around the opening may be provided. In the embodiments described, the proofing device may be designed such that it influences primarily substantially the passing of light through the opening, namely such that the light which is has been emitted or influenced by samples in wells of a microplate used in the microplate-reader may pass through the opening from the sample compartment to the appliance compartment, while other light (which has not been emitted or influenced by the samples) is blocked as completely as possible from passing through the opening.

A movement device for mixing and/or circulating gas that is present in and/or flowing into the sample compartment may be arranged in the sample compartment.

The movement device may comprise at least one of the following devices: a blower, a device comprising one or more baffle plates, an agitation device comprising one or more paddles, or a structured jet nozzle system. Thereby, the device comprising the one or more baffle plates may be arranged near by a gas inlet into the sample compartment. The agitation device comprising the one or more paddles may be arranged near by the holding device. The structured jet nozzle system may comprise a plurality of inlet nozzles, which are arranged substantially uniformly distributed in the sample compartment, so as to effect that during the inflow of gas through the inlet nozzles the gas atmosphere in the sample compartment is moved and mixed substantially uniformly. The inlet nozzles may be arranged to be distributed, preferably equally spaced, along a gas inlet line. The gas inlet line may sneak in an arrangement substantially as whole along respectively substantially parallel to a wall surface, such as ceiling or bottom wall surface, of the sample compartment. The arrangement may comprise a substantially S-shaped arrangement, a plurality of substantially S-shaped arrangements and/or a substantially spiral-shaped arrangement. Alternatively or in addition, the gas inlet line may divide or bifurcate at least in sections, in one or plural sections, into two or more gas inlet sub-lines.

The control unit may comprise a computer having, for example stored therein, corresponding software, wherein said computer may be connectable to a central computer of the microplate-reader or integrated therein. Alternatively, the control unit may comprise a computer having corresponding software, wherein this computer is connectable to a central computer of the microplate-reader and arranged in a separate housing.

The control unit may be designed to control the composition of the gas atmosphere comprising up to four, five, six or more different gases. To this end, the control unit may comprise gas sensors for measuring different gases in the sample compartment, i.e. for controlling the composition of gas atmosphere surrounding the samples-containing wells of a microplate used in this microplate-reader. Independent from this, the microplate-reader may comprise a gas inlet, in particular a gas inlet without gas sensor, whi0063h inlet is actuatable by the control unit and which is for admitting gas into the sample compartment.

At least one gas of the different gases may be selected from a group which comprises nitrogen ($N_2$), carbon dioxide ($CO_2$), oxygen ($O_2$), carbon monoxide (CO), hydrogen sulphide ($H_2S$) and sulphur dioxide ($SO_2$).

The control unit preferably comprises an $O_2$-sensor for measuring and controlling the oxygen content of the gas atmosphere surrounding the samples-containing wells of a microplate used in this microplate-reader and a $CO_2$-sensor for measuring and controlling the carbon dioxide content of the gas atmosphere surrounding the samples-containing wells of a microplate used in this microplate-reader.

Independent from this and/or further to this, the control unit may be designed to control the humidity and the temperature of the gas atmosphere. To this end, the control unit may comprise in the sample compartment a humidity sensor for measuring the humidity of the gas atmosphere and a temperature sensor for measuring the temperature of the gas atmosphere.

Independent from this and/or further to this, the control unit may comprise a cooling device for cooling and/or a heating device for heating the sample compartment. Preferably, the heating device is thereby mounted on the separating plate or on the interior housing respectively and is in heat exchange communication with the gas atmosphere in the sample compartment, and the cooling device is mounted on the bottom of the sample compartment and is in heat exchange communication with the gas atmosphere in the sample compartment. The heating device may be mounted on a plate which is arranged on the sample compartment side of the separating plate resp. on the side of the interior space of the interior housing. Preferably, the plate is connected non-heat conductingly with the separating plate resp. with the interior housing. A condensation of humidity respectively water on the microplate respectively at, on and/or in the wells of the microplate is counteracted by these arrangements of the heating device and the cooling device. What has been disclosed here with respect to the cooling device resp. the heating device applies likewise for the design of the microplate-reader having a separating plate resp. having an interior housing.

A separate ventilation device, which may be arranged in the appliance compartment, may be provided in the microplate-reader. The ventilation device serves for cooling light sources (e.g. lamps) and/or other devices which generate heat. The ventilation device may be actuated respectively operated independently from the heating device arranged in the sample compartment respectively the cooling device arranged in the sample compartment.

In the microplate-reader, the first measurement device, the second measurement device and/or the third measurement device may respectively comprise a light guide having an admission point for light and an exit point for light, and a light detector device arranged for measuring light exiting from the exit point. The first accession point for light into the first measurement device, the second accession point for light into the second measurement device and the third accession point for light into the third measurement device may respectively be arranged in the sample compartment.

Herein, the term light guide is understood to refer to an optical fiber, to an optical fiber bundle, or to a mirror system. Light guides embodied as an optical fiber or an optical fiber bundle, and a light guide embodied as a mirror system comprise an admittance point for light, an exit point for light and a light guide passage, which extends from the admittance point to the exit point and along which light can be guided by the light guide.

In the microplate-reader, a respective light guide of the first, second and/or third measurement device may be embodied as an optical fiber or an optical fiber bundle. Alternatively, a respective light guide can be embodied as a mirror system. Combinations of optical fibers and mirrors are feasible for the illumination of the samples as well as for the detection of the light coming from the samples.

The light detector device of a respective first, second and/or third measurement device may be arranged in the sample compartment or in the appliance compartment.

In the microplate-reader, the first light detector device of the first measurement device and/or the third light detector device of the third measurement device may be arranged in the sample compartment. In the microplate-reader, the second light detector device of the second measurement device designed for measuring the fluorescence in wells may be arranged in the appliance compartment.

The microplate-reader may comprise at least one illumination device designed for transilluminating respectively for irradiating samples in wells of a microplate used in the microplate-reader with light. The illumination device may comprise a light source and a light guide for guiding at least a portion of the light generated by the light source to resp. into a well of a microplate used in the microplate-reader respectively to a sample arranged in a well.

A first, second and/or third illumination device may be provided, respectively, for a respective first, second and/or third measurement device. However, it also possible to provide that an illumination device is provided in common for the first and second measurement device, the second and third measurement device, the first and third measurement device respectively in common for the first, second and third measurement device.

A respective light source of an illumination device may be selected from a group, which comprises a laser, a flash lamp, an LED (light emitting diode) and a laser diode.

In particular uses of the microplate-reader, it may be important to measure resp. to detect kinetics of the growth resp. the transformation of cell cultures which are arranged as samples in a well of a microplate. The measuring resp. detecting of the kinetics may be achieved by measuring resp. detecting, in particular a change as a function of time, of the absorbance, the fluorescence and/or the luminescence of the cell culture (sample), preferably the luminescence of the cell culture (sample).

For measuring resp. detecting kinetics that proceed temporally relatively quickly, it may be necessary, in particular advantageously, that the light source of the illumination device generates relatively short light pulses. Therefore, a pulsed laser, a flash lamp, an LED (light emitting diode) operated in a pulsed mode, and/or a laser diode operated in a pulsed mode may be light source suitably for this purpose.

A flash lamp which is not actively cooled may be provided in the microplate-reader as a light source. This flash lamp may be arranged in the appliance compartment. Further, light generated from this light source may be guided by a light guide to a sample, which as arranged in a well of a microplate used in the microplate-reader, for irradiating and/or transilluminating the sample.

The microplate-reader may comprise a first illumination device, which is designed for transilluminating samples in wells of a microplate used in the microplate-reader with light and which is arranged in the appliance compartment. Thereby, the first measurement device may be arranged in the sample compartment. The second measurement device may be arranged in the appliance compartment. The third measurement device may be arranged in the sample compartment or in the appliance compartment. Thereby, the first accession point of light into the first measurement device, the second accession point of light into the second measurement device and the third accession point of light into the third measurement device may be arranged in the sample compartment.

The microplate-reader may comprise a first illumination device, which is designed for transilluminating samples in wells of a microplate used in the microplate-reader with light. Thereby, an exit point of the first illumination device may be arranged in the sample compartment. The microplate-reader may further comprise a second illumination device, which is arranged in the appliance compartment and which is designed for irradiating samples in wells of a microplate used in the microplate-reader with light. Thereby, an exit point of the first illumination device may be arranged in the sample compartment. The second illumination device may be selected from the group, which comprises a laser, a flash lamp, an LED (light emitting diode) and a laser diode.

The first, second and/or third measurement device may comprise a first, second and/or third optical system, wherein at least one of these optical systems and/or a used (inserted) microplate are designed to be movable relative to each other in the direction of a Z-axis of a Cartesian coordinate system. Thereby, the used (inserted) microplate may be designed to be movable in the direction of the Z-axis. Alternatively resp. in addition to this, the first, second and/or third optical system may be designed to be movable in the direction of the Z-axis. Preferably, the first, second and/or third optical system is designed so that it can be lowered partly into the sample compartment through the at least one opening in the separating plate resp. in a wall, such as a ceiling wall, of the interior housing.

In the corresponding method for measuring living cells in a microplate-reader (see below) and/or in the use of a microplate-reader (see below) it may occur that a reagent is added, e.g. using an injector device, to at least one sample in at least one well of the microplate and triggers a chemical reaction. With the triggering of the chemical reaction, there may go along a luminescence reaction resp. a change of the luminescence characteristics, a change of the fluorescence and/or a change of the absorbance of the sample. These may be detected, e.g. using at least one of the measurement devices, for example by observing (measuring resp. detecting) the luminescence and/or the fluorescence and/or the absorbance of the sample.

For adding a reagent, the microplate-reader may comprise an according injector apparatus designed for adding a reagent to the samples in wells of a microplate used in the microplate-reader. The injector apparatus may dispense reagents, which may trigger a chemical reaction resp. a luminescence reaction going along therewith in a well that is currently positioned in an optical axis of the third measurement device. The observation (the measuring resp. detecting) of a chemical reaction, e.g. by observing a luminescence reaction, may be carried out in a same well substantially simultaneously with the adding of a reagent and where required in a time interval subsequent thereto. Alternatively resp. in addition to this, the observation (the measuring resp. detecting) of a chemical reaction, e.g. by observing a luminescence reaction, may also be carried out in a well which different from the well into which the reagent is currently added. In particular, this may be carried out substantially simultaneously with the adding of the reagent into a well and where required in a time interval subsequent thereto.

It is preferred to add a reagent to a sample in a well and to simultaneously observe a chemical reaction in a well spaced at a distance thereto, e.g. in a neighboring well. In this sense, it is possible to add a reagent to a sample sequentially in each well of the microplate and to simultaneously observe a chemical reaction in a well spaced at a distance thereto, e.g. in a neighboring well e.g. by observing (measuring resp. detecting) the luminescence and/or the fluorescence and/or the absorbance of the sample contained in the well spaced at a distance, e.g. the neighboring well. By this procedure it is possible to "stimulate" one well (i.e. to add a reagent to the sample contained therein) of the microplate after the other and to observe (measure resp. detect) delayed by a time period the chemical reaction caused by the stimulation. This time period of the time delay is determined by the geometrical offset (i.e. lateral distance in an X-Y-plane) between the respective wells spaced at a distance, e.g. the respective neighboring wells, and the velocity by which the microplate and the measurement device used for observing the chemical reaction (more precisely: the optical axis thereof) are moved relative to each other, in particular in a plane that is parallel to the microplate.

This object is achieved with respect to a second aspect by the features as herein disclosed. Thereby, there is provided a method for measuring living cells in a microplate reader which comprises a housing surrounding an interior space. The method comprises the following steps:
a) providing a sample compartment, which is separated from an appliance compartment and in which a holding device for accommodating of at least one microplate is arranged,
   a1) wherein a separating plate is arranged in the housing so as to subdivide the interior space of the housing into the sample compartment and the appliance compartment, or
   a2) wherein an interior housing, in which the holding device is arranged, is provided within the housing, and wherein the separating plate or the interior housing has at least one opening which is designed such that light emitted or influenced by samples in wells of a microplate used or inserted in the microplate-reader can pass therethrough from the sample compartment to the appliance compartment,
b) accommodating in a holding device of said microplate reader of at least one microplate comprising wells containing samples,
c) positioning of the samples-containing wells of this(these) microplate(s) in relation to at least one measuring device of this microplate reader,
d) controlling the composition of the gas atmosphere in the sample compartment, and
e) using this at least one measuring device for detecting light,
   which is emitted by samples in wells of a microplate used or inserted in this microplate reader, and/or
   which is influenced by samples transilluminated by light in wells of a microplate used or inserted in this microplate reader.

In this method, the sequence of steps, particularly steps b) to e), may be changed. Thus for example, the step d) may be executed prior to the step c) or to the step b) and/or the step e) may be executed prior to the step c) or prior to the step d).

The method may further comprise at least one or more of the following steps:
f) measuring light, which is influenced by samples that are transilluminated by light in wells of a microplate used in the microplate-reader, for measuring the absorbance of the sample,
g) measuring light, which is emitted from samples that are irradiated by light in wells of a microplate used in the microplate-reader, for measuring the fluorescence of the sample, and
h) measuring light, which is emitted from samples that are irradiated by light in wells of a microplate used in the microplate-reader, for measuring the luminescence of the sample.

A defined gas atmosphere may be adjusted in the sample compartment and at least one or more of the steps f), g) and h) mentioned hereinbefore may be executed with resp. under the adjusted gas atmosphere of the step d) mentioned above.

In the method, gas which is flowing into the sample compartment and/or which is present therein may be mixed and/or circulated by means of a movement device arranged in the samples compartment.

In the method, the composition of the gas atmosphere in the sample compartment may be controlled by means of a control unit. Thereby, gas may be admitted into the sample compartment through a gas inlet, wherein the gas inlet is actuated by the control unit. In the method, the proportion in the gas atmosphere in the sample compartment of at least one particular gas out of different gases may be controlled, wherein the particular gas is selected from a group, which comprises nitrogen ($N_2$), carbon dioxide ($CO_2$), oxygen ($O_2$), carbon monoxide (CO), hydrogen sulphide ($H_2S$) and sulphur dioxide ($SO_2$). In the method, the humidity and/or the temperature of the gas atmosphere in the sample compartment may be controlled by means of the control unit. In the method, in the sample compartment, the air may be ventilated by means of a ventilation device.

In the method for measuring living cells and/or in the use of a microplate-reader (see below), a reagent may be added to at least one sample in at least one well of the microplate by means of an injector apparatus. Thus, a chemical reaction may be caused, which can be detected by means of at least one of the measurement devices. In particular, thereby going along with the chemical reaction, a luminescence reaction resp. a change of the luminescence characteristics and/or a change in the fluorescence and/or a change in the absorbance of the sample. For example, a reagent may be added in a well, which is currently in an optical axis of the third measurement device, and may cause a chemical reaction there.

The observation (the measuring resp. detecting) of a chemical reaction, e.g. by observing the luminescence reaction caused, may be carried out in a same well substantially simultaneously with the adding of a reagent and where required in a time interval subsequent thereto. Alternatively resp. in addition to this, the observation (the measuring resp. detecting) of a chemical reaction, e.g. by observing the luminescence reaction caused, may also be carried out in a well which different from the well into which the reagent is currently added. In particular, this may be carried out substantially simultaneously with the adding of the reagent into a well and where required in a time interval subsequent thereto.

As already pointed out, it is preferred to add a reagent to a sample in a well and to simultaneously observe a chemical reaction in a well spaced at a distance thereto, e.g. in a neighboring well.

A chemical reaction in the sample (e.g. a cell culture) caused by adding a reagent resp. a cell culture may be observed resp. identified by observing (measuring resp. detecting) a kinetics of the growth resp. the change of a sample resp. the cell culture arranged in a well of a microplate. In the method, samples in wells of a microplate used in (inserted into) the microplate-reader may be transilluminated by light and/or samples in wells may be irradiated by light by means of an illumination device.

Samples in wells of the microplate used in the microplate-reader may also be irradiated by light by means of a second illumination device. The second illumination device may be arranged in the appliance compartment. It may preferably be selected from a group, which comprises a laser, a flash lamp, an LED (light emitting diode) and a laser diode. In the method, the absorbance of a sample and/or the fluorescence of a sample and/or the luminescence of a sample may be measured respectively by means of a measurement device arranged in the sample compartment or in the appliance compartment. In particular, the absorbance of the sample may be measured by means of a first measurement device arranged in the sample compartment and/or the fluorescence of the sample may be measured by means of a second measurement device arranged in the appliance compartment. Also, the luminescence of the sample may be measured by means of a third measurement device arranged in the sample compartment or in the appliance compartment.

In the microplate-reader in which the method can be performed, the control unit may comprise an $O_2$-sensor and/or a $CO_2$-sensor for controlling the oxygen content and/or carbon dioxide content of the gas atmosphere surrounding the samples-containing wells of a microplate used in (inserted into) this microplate reader.

Thereby, the oxygen concentration and/or the carbon dioxide concentration of this gas atmosphere may be held at a defined value by selectively admitting carbon dioxide and/or nitrogen during the measurement of microaerophilic, optionally anaerobic and obligatorily anaerobic microorganisms, fungi or eukaryotic cells. It is feasible in the method described above that:

d1) when controlling the composition of the gas atmosphere in the sample compartment, the concentration of a gas which is already present in the gas atmosphere, such as oxygen ($O_2$) or carbon dioxide ($CO_2$), may be lowered by admitting a chemically inactive gas, such as nitrogen or an inert gas, into the sample compartment (whereby in particular the gas atmosphere including the gas which is already present is "diluted" resp. partially squeezed out) and measuring the concentration of the gas which is already present by means of a sensor, such as an $O_2$-sensor and/or a $CO_2$-sensor, which is responsive to this gas which is already present, or d2) when controlling the composition of the gas atmosphere in the sample compartment, the concentration of a gas which is already present in the gas atmosphere, such as oxygen ($O_2$) or carbon dioxide ($CO_2$), may be raised by admitting more of this gas into the sample compartment (whereby in particular the concentration of this gas is selectively raised) and measuring the concentration of this gas by means of a sensor, which is responsive to this gas, or d3) when controlling the composition of the gas atmosphere in the sample compartment, the concentration of a gas which is not yet or already present in the gas atmosphere, such as hydrogen sulphide ($H_2S$) or carbon monoxide (CO), may be raised by admitting more of this gas into the sample compartment (whereby in particular the concentration of this gas is selectively raised) and measuring the concentration of this gas by means of a sensor, which is responsive to this gas.

This object mentioned above is achieved with respect to a third aspect by the use according to the invention of the aforementioned microplate reader according to the invention or by the aforementioned method according to the invention. These uses concern the measurement of living cells in a microplate reader, wherein the living cells are chosen from a group which comprises microaerophilic, optionally anaerobic and obligatorily anaerobic microorganisms, fungi and eukaryotic cells.

Additional inventive features are provided by the respective dependent claims.

The use of such a microplate reader is especially preferred in the measurement of microaerophilic or facultative anaerobic microorganisms in a defined $O_2$ concentration. Methods for the measurement of living cells in a microplate reader are also preferable, with the living cells being chosen from a group which comprises microaerophilic, facultative anaerobic and mandatorily anaerobic microorganisms, as well as fungi and eukaryotic cells. Multi-well plates or microtiter plates according to the ANSI-SBS Standard 2004 are designated as microplates which can comprise 6, 12, 24, 48, 96, 384 or 1536 wells for example.

The microplate reader in accordance with the invention comprises the following advantages:

The microplates with the samples to be measured need not permanently be transferred back and forth between an incubator and the measuring device. Such transfers can therefore be omitted during which the cells or the cell cultures are subjected to ambient air and can be influenced by such ambient air in such a way that distorted measuring results will be obtained.

The measurements with respect to luminescence and/or fluorescence and/or absorbance can occur in a fully automated manner, so that after the charging of the microplate reader in accordance with the invention it is no longer necessary that an operator be present.

In contrast to conventional (e.g. $CO_2$) incubators without integrated fluorescence measurement, long-term measurements can be performed with a microplate reader in accordance with the invention, thus preventing the occurrence of so-called "night windows" during which no data can be detected.

The control of the $O_2$ and/or $CO_2$ concentration in the atmosphere above the wells or in the ambient environment of the wells of microplates enable the measurement of microaerophilic, facultative anaerobic or mandatorily anaerobic microorganisms, fungi or eukaryotic cells under a defined $O_2$ and/or $CO_2$ concentration.

BRIEF INTRODUCTION OF THE DRAWINGS

The microplate reader in accordance with the invention and its use in accordance with the invention will now be explained by reference to the schematic illustrations which show exemplary and preferred embodiments without limiting the scope of the present invention, wherein.

Figure 7:
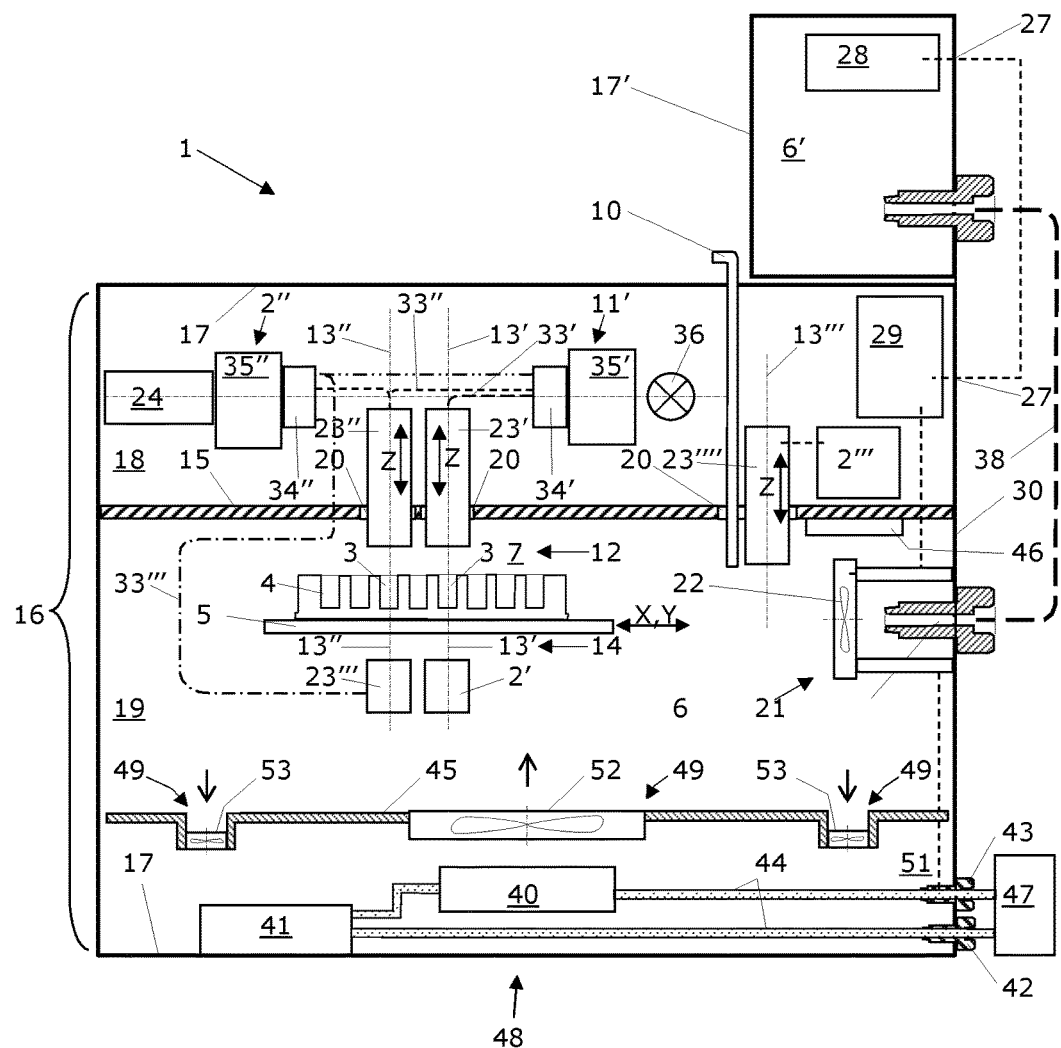
Figure 8:
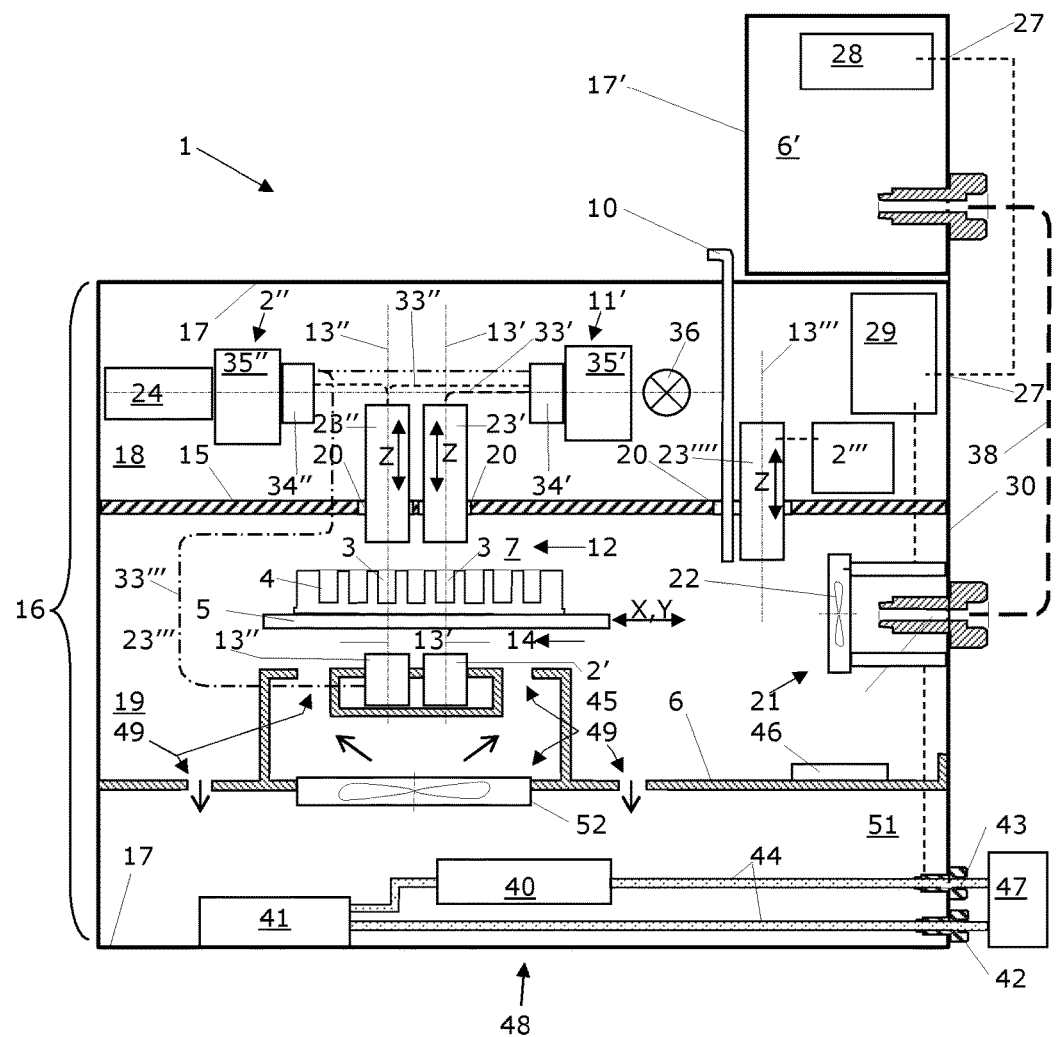

FIG. 7 shows a highly schematic vertical sectional view through a microplate reader in accordance with the invention according to a further preferred embodiment, comprising an interior space of the housing which is subdivided by means of a separating plate into an appliance compartment and a sample compartment, and further comprising a heating device and a cooling device, and a support element for the heat exchange communication;

FIG. 8 shows a highly schematic vertical sectional view through a microplate reader in accordance with the invention according to another further embodiment, comprising an interior space of the housing which is subdivided by means of a separating plate into an appliance compartment and a sample compartment, further comprising the heating device and the cooling device, and a support element for the heat exchange communication in an alternative embodiment.

DETAILED DESCRIPTION OF THE INVENTION

Figure 1:
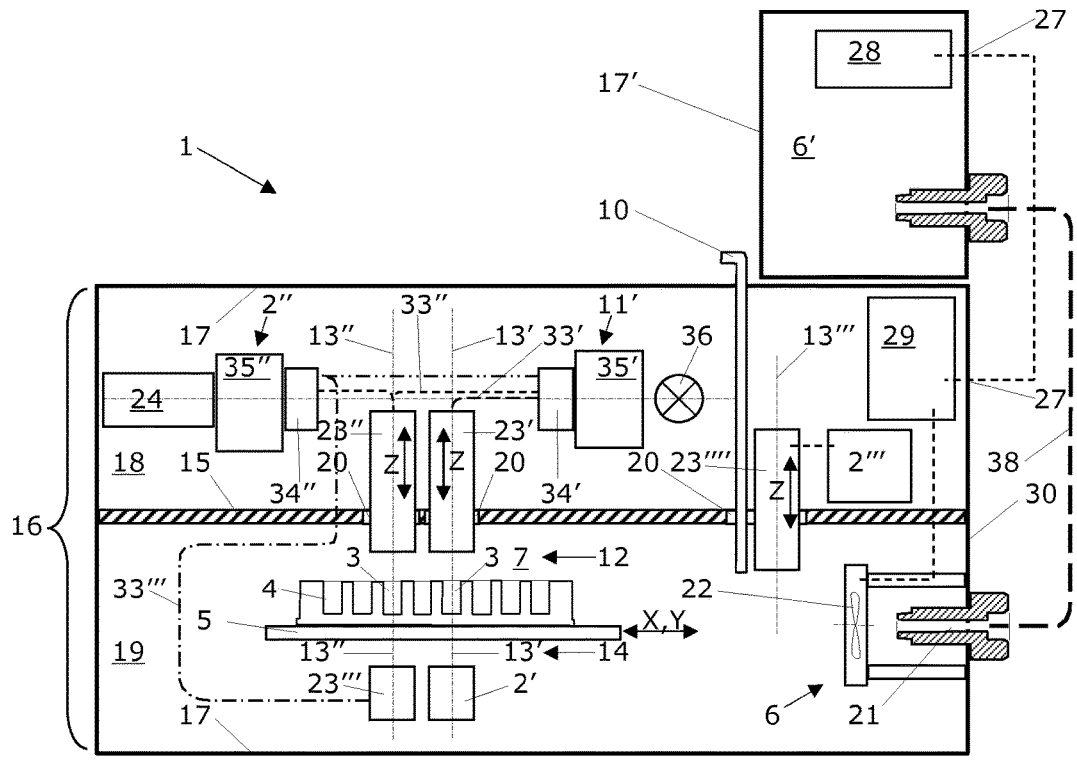
FIG. 1 shows a highly schematic vertical sectional view through a microplate reader in accordance with the invention according to a preferred first embodiment, comprising an interior space of the housing which is subdivided by means of a separating plate into an appliance compartment and a sample compartment.

FIG. 1 shows a highly schematic vertical sectional view through a microplate reader 1 in accordance with the invention according to a preferred first embodiment, comprising a housing 17 whose interior space 16 is subdivided into an appliance compartment 18 and a sample compartment 19 by means of a separating plate 15. This microplate reader 1 comprises at least one measuring device 2', 2", 2'" for the detection of light.

FIG. 1 shows a first measuring device 2' according to a first variant of the microplate reader 1 in accordance with the invention, with which light can be measured which was influenced by samples transilluminated by light in wells 3 of a microplate 4 used in this microplate reader 1 (therefore the absorbance of the sample). This first measuring device 2' is preferably arranged in the sample compartment 19 of the microplate reader 1 and a first illumination device 11' for transilluminating the samples in the wells 3 of a microplate 4 is preferably arranged in the appliance compartment 18 of microplate reader 1. As a result, the first measuring device 2' for detecting light which is influenced by samples in wells 3 of a microplate 4 used in this microplate reader 1 is arranged on a second side 14 (i.e. the bottom side) of a microplate 4 inserted in this microplate reader 1 and in the direction of a first optical axis 13'. Consequently, the first illumination device 11' for transilluminating the samples is arranged on a first side 12 (i.e. on the upper side) of a microplate 4 inserted in this microplate reader 1 and also in the direction of this first optical axis 13'. The assignment of the first illumination device 11' to the first optical axis 13' occurs in this case with a first fiber-optical line 33'. The first illumination device 11' comprises a first fiber slide 34', a first wavelength-selective monochromator 35' and a flash lamp 36. As a result, the light of the flash lamp 36 is guided for the transillumination of the samples by means of the first fiber-optical line 33' in the direction of the first optical axis 13' and via a first optical system 23' against the samples. Said first optical system 23' can be arranged to be height-adjustable in the direction of a Z-axis of a Cartesian system of coordinates (cf. double arrow Z). In this case, a holding device 5 for accommodating at least one microplate 4 and for positioning the wells 3 of these microplate(s) 4 in relation to the first measuring device 2' and thereby also in relation to the first optical axis 13' is arranged between the first illumination device 11' and the first measuring device 2', but preferably in the sample compartment 19.

A second measuring device 2" is shown in FIG. 1 according to a second variant of the microplate reader 1 in accordance with the invention, with which light can be measured with respect to a second optical axis 13", which light is emitted by samples in wells 3 of a microplate 4 used in this microplate reader 1 (therefore the fluorescence of the sample). Said second measuring device 2" comprises a photo multiplier tube (PMT) 24, a second wavelength-selective monochromator 35" and a second fiber slide 34". For the purpose of this fluorescence measurement the first illumination device 11' of the microplate reader 1 is used for irradiating (exciting) the samples in the wells 3 of a microplate 4. The assignment of the first illumination device 11' to the second optical axis 13" occurs in this case by way of a second fiber-optical line 33" and by way of a second optical system 23". Said second optical system 23" can be arranged to be height-adjustable in the direction of a Z-axis of a Cartesian system of coordinates (cf. double arrow Z). As a result, the light of the flash lamp 36 is guided for irradiating the samples by means of the second fiber-optical line 33" into the direction of the second optical axis 13".

Two different arrangements can be used for detecting the fluorescence emitted by the samples:

In the so-called "top reading" the second optical system 23" is used above the microplate 4 which is connected by way of the second fiber-optical line 33" with the second fiber slide 34", so that the photo multiplier tube (PMT) 24 can be used for detecting the fluorescence of every single sample in a well 3 of the microplate 4.

In the so-called "bottom reading" there is a third optical system 23'" beneath the microplate 4 and is connected by way of a third fiber-optical line 33'" with the first and second fiber slide 34', 34", so that this illumination device 11' and the same measuring device 2" can be used for exciting and detecting the fluorescence of every single sample in a well 3 of the microplate 4.

In this case, the holding device 5 for accommodating at least one microplate 4 and for positioning the wells 3 containing the samples of these microplate(s) 4 is preferably arranged with respect to the first or second measuring device 2', 2" in the sample compartment 19 and beneath the first illumination device 11' which is preferably housed in the appliance compartment 18.

A third measuring device 2'" is shown in FIG. 1 according to a third variant of the microplate reader 1 in accordance with the invention, with which light can be measured which is emitted by samples in wells 3 of a microplate 4 used in this microplate reader 1 (i.e. the luminescence of the sample). A third measuring device 2' is used for this luminescence measurement, which measuring device is preferably arranged in the appliance compartment 18 of the microplates reader 1 and with respect to a third optical axis 13'". A generally known injector apparatus 10 which preferably reaches into the sample compartment 19 of the microplate reader 1 is used for triggering a chemical reaction which goes along with a luminescence reaction resp. a change in the luminescence characteristics, and/or a change in the fluorescence and/or a change in the absorbance in or on the samples in the wells 3 of a microplate 4. Said injector apparatus 10 is preferably configured and arranged in such a way that the reagents triggering the chemical reaction, e.g. a luminescence reaction, can be added in a well 3 of the microplate 4, when the well 3 is disposed at the time on a third optical axis 13'" and thereby precisely above the third measuring device 2'".

A preferred embodiment of the microplate-reader 1 is designed such that a reagent is added to a sample in a well 3 and a chemical reaction is simultaneously observed in a well spaced at a distance thereto, e.g. in a neighboring well. In this sense, it is possible to add a reagent to a sample sequentially in each well 3 of the microplate 4 and to simultaneously observe a chemical reaction in a well 3 spaced at a distance thereto, e.g. in a neighboring well e.g. by observing (measuring resp. detecting) the luminescence and/or the fluorescence and/or the absorbance of the sample contained in the well spaced at a distance, e.g. the neighboring well. By this procedure it is possible to "stimulate" one well (i.e. to add a reagent to the sample contained therein) of the microplate 4 after the other and to observe (measure resp. detect) delayed by a time period the chemical reaction caused by the stimulation. This time period of the time delay is determined by the geometrical offset (i.e. lateral distance in an X-Y-plane) between the wells 3 respectively concerned (spaced at a distance, e.g. neighboring) and the velocity by which the microplate 4 and the measurement device 2', 2", 2''' (resp. the optical axis 13', 13", 13''' thereof) used for observing the chemical reaction are moved relative to each other, in parallel to particular the X-Y-plane.

Figure 2:
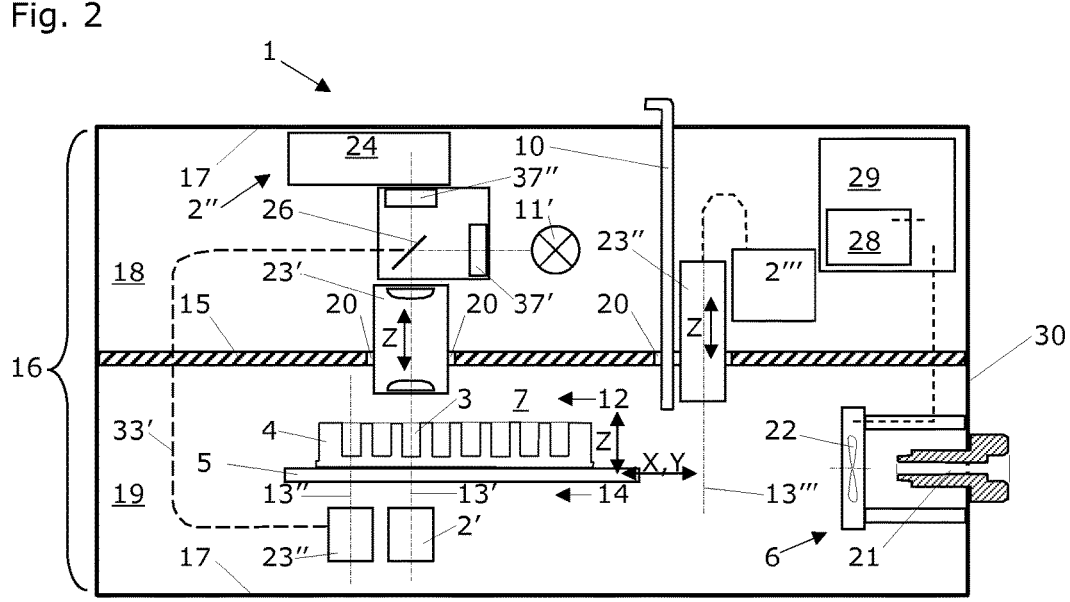
FIG. 2 shows a highly schematic vertical sectional view through a microplate reader in accordance with the invention according to a preferred second embodiment, comprising an interior space of the housing which is subdivided by means of a separating plate into an appliance compartment and a sample compartment.
Figure 3:
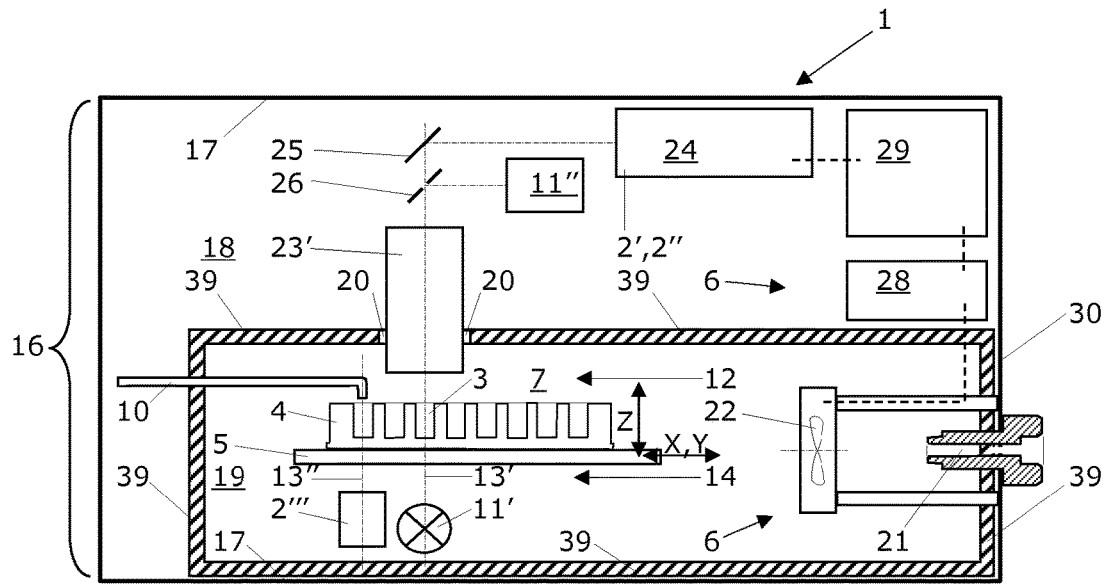
FIG. 3 shows a highly schematic vertical sectional view through a microplate reader in accordance with the invention according to a preferred third embodiment, comprising an interior space of the housing which is subdivided by means of a separating plate into an appliance compartment and a sample compartment.

An according injector apparatus 10 is also conceived in the embodiments of a microplate-reader shown in the FIGS. 2 and 3, and what has been disclosed hereinbefore with respect to the injector apparatus 10 and its function resp. use applies also to the embodiments shown there.

The third measuring device 2''' preferably comprises a fourth optical system 23'''', which can movably be arranged in the direction of a Z-axis of a Cartesian system of coordinates (cf. double arrow Z). The first, second, third and fourth optical systems 23', 23", 23''' and 23'''' are arranged in an especially preferred way to be partly lowerable into the sample chamber 19 through a respective opening 20 in the separating plate 15.

Figure 4:
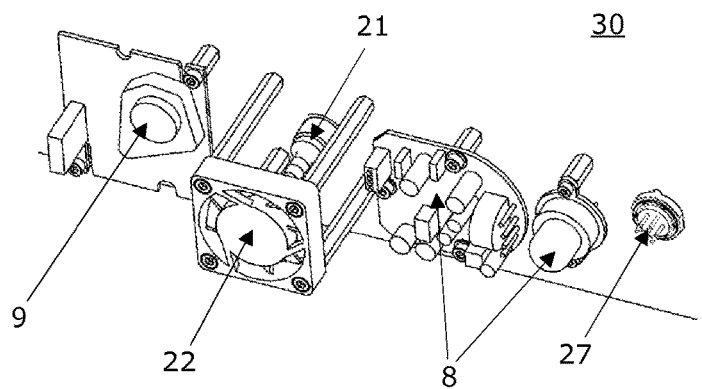
FIG. 4 shows an exemplary arrangement of an $O_2$ sensor, a $CO_2$ sensor, a fan and the gas inlet on the inside of the rear wall of a microplate reader in accordance with the invention.

A separate control unit 6' is placed on the housing 17 of the microplate reader 1 in accordance with the invention, with the arrangement of an $O_2$ sensor 8, a $CO_2$ sensor 9, a fan 22 and a gas inlet 21 being provided on the inside of the rear wall 30 of the housing 17 of the microplate reader 1 in accordance with the invention (cf. FIG. 4). The control unit 6 of the microplate reader 1 preferably comprises an $O_2$ sensor 8 for measuring and controlling the oxygen content of the gas atmosphere 7 in the sample compartment 19, i.e. in the surrounding of the wells 3 containing the samples of microplates for inserted in said microplate reader 1. The control unit 6 of the microplate reader 1 comprises in an especially preferred way and alternatively to or in addition to this $O_2$ sensor 8 a $CO_2$ sensor 9 for measuring and controlling the carbon dioxide content of the gas atmosphere 7 surrounding the wells 3 containing the samples of microplate(s) 4 inserted in said microplate reader 1. The control unit 6 is therefore arranged partly within and partly without the housing 17 of the microplate reader 1 and is or can be connected by way of electrical contacts 27 and gas lines 38 with the microplate reader 1. The separate control unit 6' is directly connected to the necessary pressure cylinders for the gas is to be used. The respective valves and throttles for the required gas connections are installed in the separate control unit 6' (not shown). Alternatively, it is also possible to use mouse and throttles on the gas pressure cylinders, wherein these valves are preferably arranged as electrically controlled solenoid valves (of the type normally closed). FIG. 1 does not show among other things the control elements, display elements and power supplies for the separate control unit 6' and the microplate reader 1.

FIG. 2 shows a highly schematic vertical sectional view through a microplate reader 1 in accordance with the invention according to a preferred second embodiment, comprising a housing 17 whose interior space 16 is subdivided into an appliance compartment 18 and a sample compartment 19 by means of a separating plate 15. This microplate reader 1 comprises at least one measuring device 2', 2", 2''' for the detection of light.

FIG. 2 shows a first measuring device 2' according to a first variant of the microplate reader 1 in accordance with the invention, with which light can be measured which was influenced by samples transilluminated by light in wells 3 of a microplate 4 used in this microplate reader 1 (therefore the absorbance of the sample). This first measuring device 2' is preferably arranged in the sample compartment 19 of the microplate reader 1 and a first illumination device 11' for transilluminating the samples in the wells 3 of a microplate 4 is preferably arranged in the appliance compartment 18 of microplate reader 1. As a result, the first measuring device 2' for detecting light which is influenced by samples in wells 3 of a microplate 4 used in this microplate reader 1 is arranged on a second side 14 (i.e. the bottom side) of a microplate 4 inserted in this microplate reader 1 and in the direction of a first optical axis 13'. Consequently, the first illumination device 11' for transilluminating the samples is arranged on a first side 12 (i.e. on the upper side) of a microplate 4 inserted in this microplate reader 1 and also in the direction of this first optical axis 13'. The assignment of the first illumination device 11' to the first optical axis 13' occurs in this case with a partly transparent (e.g. 50%) mirror 26 or a dichroic mirror. The first illumination device 11' comprises a first wavelength-selective filter 37' and a flash lamp 36. As a result, the light of the flash lamp 36 is guided for the transillumination of the samples by means of the partly transparent mirror 26 in the direction of the first optical axis 13' and via a first optical system 23' against the samples. Said first optical system 23' can be arranged to be height-adjustable in the direction of a Z-axis of a Cartesian system of coordinates (cf. double arrow Z). In this case, a holding device 5 for accommodating at least one microplate 4 and for positioning the wells 3 of these microplate(s) 4 in relation to the first measuring device 2' and thereby also in relation to the first optical axis 13' is arranged between the first illumination device 11' and the first measuring device 2', but preferably in the sample compartment 19.

A second measuring device 2" is shown in FIG. 2 according to a second variant of the microplate reader 1 in accordance with the invention, with which light can be measured with respect to a first or second optical axis 13', 13", which light is emitted by samples in wells 3 of a microplate 4 used in this microplate reader 1 (therefore the fluorescence of the sample). Said second measuring device 2" comprises a photo multiplier tube (PMT) 24 and a second wavelength-selective filter 37". For the purpose of this fluorescence measurement the first illumination device 11' of the microplate reader 1 is used again for irradiating (exciting) the samples in the wells 3 of a microplate 4. The assignment of the first illumination device 11' to the second optical axis 13" occurs in this case again by way of a partly transparent (e.g. 50%) mirror 26 or a dichroic mirror and by way of the first optical system 23'.

Two different arrangements can be used for detecting the fluorescence emitted by the samples:
  In the so-called "bottom reading" there is a second optical system 23" beneath the microplate 4 which is connected by way of a first fiber-optical line 33' with the partly transparent mirror 26 and the second filter 37", so that the photomultiplier tube (PMT) 24 can be used for detecting the fluorescence of every single sample in a well 3 of the microplate 4.
  In the so-called "top reading" the first optical system 23' is used above the microplate 4 which is connected by way of the partly transparent mirror 26 with the second filter 37", so that the same photo multiplier tube (PMT) 24 can be used for detecting the fluorescence of every single sample in a well 3 of the microplate 4.

In this case, the holding device 5 for accommodating at least one microplate 4 and for positioning the wells 3 containing the samples of these microplate(s) 4 is preferably arranged with respect to the first or second measuring device 2', 2" in the sample compartment 19 and beneath the first illumination device 11' which is preferably housed in the appliance compartment 18.

A third measuring device 2''' is shown in FIG. 2 according to a third variant of the microplate reader 1 in accordance with the invention, with which light can be measured which is emitted by samples in wells 3 of a microplate 4 used in this microplate reader 1 (e.g. the luminescence of the sample). A third measuring device 2''' is used for this luminescence measurement, which measuring device is preferably arranged in the appliance compartment 18 of the microplates reader 1 and with respect to a third optical axis 13'''. A generally known injector apparatus 10 which preferably reaches into the sample compartment 19 of the microplate reader 1 is used for triggering a chemical reaction, with which there may go along a luminescence reaction resp. a change in the luminescence characteristics, and/or a change in the fluorescence and/or a change in the absorbance in or on the samples in the wells 3 of a microplate 4. Said injector apparatus 10 is preferably configured and arranged in such a way that the reagents triggering the chemical reaction, e.g. a luminescence reaction, can be added in a well 3 of the microplate 4, when the well 3 is disposed at the time on the third optical axis 13''' and thereby precisely above the third measuring device 2'''. The third measuring device 2''' preferably comprises a third optical system 23''' which can movably be arranged in the direction of a Z-axis of a Cartesian system of coordinates (cf. double arrow Z). The first and second optical systems 23', 23" are arranged in an especially preferred way to be partly lowerable into the sample chamber 19 through a respective opening 20 in the separating plate 15.

The same control unit 6 is preferably used in all aforementioned variants of the microplate reader 1 in accordance with the invention.

FIG. 3 shows a highly schematic vertical sectional view through a microplate reader 1 in accordance with the invention according to a preferred third embodiment, comprising a housing 17 whose interior space 16 is subdivided into an appliance compartment 18 and a sample compartment 19 by means of an interior housing 39. This microplate reader 1 comprises at least one measuring device 2', 2", 2''' for the detection of light. The interior housing 39 comprises an opening 20, which is designed such that light emitted or influenced by samples in wells 3 of a microplate 4 used in the microplate-reader 1 may pass therethrough from the samples compartment 19 into the appliance compartment 18.

FIG. 3 shows a first measuring device 2' according to a first variant of the microplate reader 1 in accordance with the invention, with which light can be measured which was influenced by samples transilluminated by light in wells 3 of a microplate 4 used in this microplate reader 1 (therefore the absorbance of the sample). This first measuring device 2' is preferably arranged in the appliance compartment 18 of the microplate reader 1 and a first illumination device 11' for transilluminating the samples in the wells 3 of a microplate 4 is preferably arranged in the sample compartment of the microplate reader 1. As a result, the first measuring device 2' for detecting light which is influenced by samples in wells 3 of a microplate 4 used in this microplate reader 1 is arranged on a first side 12 (i.e. the upper side) of a microplate 4 inserted in this microplate reader 1 and in the direction of a first optical axis 13'. Consequently, the first illumination device 11' for transilluminating the samples is arranged on a second side 14 (i.e. on the bottom side) of a microplate 4 inserted in this microplate reader 1 and also in the direction of this first optical axis 13'. The first measuring device 2' preferably comprises a mirror 25 for deflecting the light coming from the samples in the direction of a photo multiplier tube or PMT 24. Alternatively, the light coming from the samples can be supplied by means of the fiber optics of the PMT 24 (not shown). Similarly, the first illumination device 11' can be arranged as a lamp and be arranged on the first optical axis 13'. Alternatively, the light for transilluminating the samples can be guided by means of mirrors or fiber optics (both not shown) in the direction of the first optical axis 13'. In this case, a holding device 5 for accommodating at least one microplate 4 and for positioning the wells 3 containing the samples of these microplate(s) 4 is preferably arranged with respect to the first measuring device 2' between the first illumination device 11' and the first measuring device 2', but preferably in the sample compartment 19.

A second measuring device 2" is shown in FIG. 3 according to a second variant of the microplate reader 1 in accordance with the invention, with which light can be measured which is emitted by samples in wells 3 of a microplate 4 used in this microplate reader 1 (therefore the fluorescence of the sample). For the purpose of this fluorescence measurement the first measuring device 2' of the microplate reader 1 is used again which is identical in this case with the second measuring device 2". A second illumination device 11" (preferably a laser, a flash lamp or a laser diode) is used as a source for the required exciting light for irradiating the samples in the wells 3 of a microplate 4. Said second illumination device 11" is preferably arranged in the housing space 18 of the microplate reader 1. As a result, both the first measuring device 2' for the detection of light which is emitted by samples in wells 3 of a microplate 4 inserted in this microplate reader 1 and also the second illumination device 11" are disposed on the same side 12 (therefore on the upper side) of a microplate 4 inserted in this microplate reader 1. The second illumination device 11" preferably comprises a partly (e.g. 50%) transparent mirror 26 or a dichroic mirror for deflecting the exciting light in the direction of the first optical axis 13' and therefore onto or into the samples. In this case, the holding device 5 for accommodating at least one microplate 4 and for positioning the wells 3 containing the samples of these microplate(s) 4 is preferably arranged with respect to the first measuring device 2' in the sample compartment 19 and beneath the second illumination device 11" and the first measuring device 2' which are preferably housed in the appliance compartment 18.

A third measuring device 2''' is shown in FIG. 3 according to a third variant of the microplate reader 1 in accordance with the invention, with which light can be measured which is emitted by samples in wells 3 of a microplate 4 used in this microplate reader 1 (i.e. the luminescence of the sample). A third measuring device 2''' is used for this luminescence measurement, which third measuring device is preferably arranged in the sample compartment 19 of the microplate reader 1 and with respect to a second optical axis 13". A generally known injector apparatus 10 which is preferably arranged in the sample compartment 19 of the microplate reader 1 is used for triggering a chemical reaction, with which there may go along a luminescence reaction resp. a change in the luminescence characteristics, a change in the fluorescence and/or a change in the absorbance in or on the samples in the wells 3 of a microplate 4. Said injector apparatus 10 is for example configured and arranged in such a way that the reagents triggering the chemical reaction, e.g. a luminescent reaction, can be added in a well 3 of the microplate 4, when the well 3 is disposed at the time on the second optical axis 13" and thereby precisely above the third measuring device 2'''. In this case, the holding device 5 for accommodating at least one microplate 4 and for positioning the wells 3 containing the samples of these microplate(s) 4 is preferably arranged with respect to the second measuring device 2" in the sample compartment 19, beneath the injector apparatus 10 and above the third measuring device 2'''. The first measuring device 2' preferably comprises a first optical system 23' which can movably be arranged in the direction of a Z-axis of a Cartesian system of coordinates. The first optical system 23' is arranged in an especially preferred way to be partly lowerable into the sample chamber 19 through a respective opening 20 in the interior housing 39, according to the first embodiment as shown in FIG. 3.

The microplate 4 resp. the holding device 5 is movable in the direction of a Z-axis of a Cartesian coordinate system (cf. double arrow Z in FIGS. 2 and 3) relative to the first, second and/or third optical system 23', 23", 23''', respectively, of the first, second and/or third measurement device 2', 2", 2'''. The microplate 4 resp. the holding device 5 (cf. double arrow X, Y) and/or the first, second and/or third measurement device 2', 2", 2''' resp. their respective first, second and/or third optical system 23', 23", 23''' may also be designed to be movable in the direction of an X-axis and/or a Y-axis of a Cartesian coordinate system. This applies for all embodiments shown and variants of the microplate-reader 1 according to the invention and possible modifications thereof.

Preferably, all embodiments and variants of the microplate reader 1 in accordance with the invention are characterized in that the microplate reader 1 comprises a control unit 6 for controlling the composition of a gas atmosphere 7 surrounding the wells 3 containing the samples of microplates 4 inserted in this microplate reader 1. Moreover, the holding device 5 is arranged to be movable preferably in the direction of an X-axis and Y-axis of a Cartesian system of coordinates (cf. FIGS. 1 to 3: double arrows X, Y).

FIG. 4 shows an exemplary arrangement of an $O_2$ sensor 8, a $CO_2$ sensor 9, a fan 22 and a gas inlet 21 on the inside of the rear wall 30 of the housing 17 of a microplate reader 1 in accordance with the invention. The control unit 6 of the microplate reader 1 preferably comprises an $O_2$ sensor 8 for measuring and controlling the oxygen content of the gas atmosphere 7 surrounding the wells 3 containing the samples of the microplates 4 inserted in this microplate reader 1. The control unit 6 of the microplate reader 1 comprises in an especially preferred way a $CO_2$ sensor 9 alternatively to or in addition to said $O_2$ sensor 8 for measuring and controlling the carbon dioxide content of the gas atmosphere 7 surrounding the wells 3 containing the samples of microplate(s) 4 inserted in this microplate reader 1. This control unit 6 can be arranged partly outside of the housing 17 of the microplate reader 1 and can be connected or connectable for example by way of electric contacts 27 and gas conduits (not shown) with the microplate reader 1 (not shown). It can also be provided however that the control unit 6 is integrated completely in the microplate reader 1 and is housed in a common housing 17 (cf. FIGS. 2 and 3). In this case, the microplate reader 1 would be connected directly to the necessary pressure cylinders for the gases to be used (cf. FIGS. 2 and 3). Preferably, the respective valves and throttles are then also installed in the housing 17 of the microplate reader 1 (not shown). Alternatively, valves and throttles on the gas pressure cylinders can also be used, with these valves being arranged as electrically controlled solenoid valves (of the type normally closed) (not shown).

The control unit preferably comprises a computer 28 with respective software. In this case, the computer 28 can be connected with a central computer 29 of the microplate reader 1 (cf. FIG. 1) (housed in a separate housing 17' for example) or be integrated in this central computer 29 of the microplate reader 1 (not shown).

Preferably, the nitrogen ($N_2$) and/or the carbon dioxide ($CO_2$) to be used for displacing the ambient air are provided in pressure cylinders, with generally known control valves and throttles be used in these pressure cylinders in order to set the required feed pressure for these gases. Such process gases can alternatively also be obtained from other sources (e.g. from in-house conduits). In addition to nitrogen and carbon dioxide, other gases can be used for producing a defined percentage in the atmosphere usually prevailing in the sample compartment (combined with respective gas detectors in the sample compartment 19). By observing the potentially applicable safety measures it is therefore also possible to introduce other gases such as noble gases or inert gases (e.g. argon) or also reactive or poisonous gases (e.g. oxygen, carbon monoxide, hydrogen sulfide or sulfur dioxide) into the sample compartment 19 of the microplate reader 1 by way of a gas inlet 21 via a microplate 4 inserted in the area of the wells 3 in said microplate reader 1 for generating a specific composition of the gas atmosphere. Preferably, the control unit 6 is equipped with sufficient gas conduits and control valves so that even more complex gas compositions with several gas components are enabled.

With respect to suitable $CO_2$ sensors, the currently used $CO_2$ sensor shall be mentioned: SenseAir® $CO_2$ Engine® ICB, Part No.: 033-9-0001 of SenseAir AB in SE820 60 Delsbo, Sweden. With respect to suitable $O_2$ sensors, the currently used $O_2$ sensor shall be mentioned: Pewatron FCX-MEP2-F—CH oxygen module of Pewatron AG in CH-8052 Zurich, Switzerland.

The control unit 6 in combination with an $O_2$ sensor allows controlling the oxygen content of the gas atmosphere 7 surrounding the wells 3 containing the samples of microplate(s) 4 inserted in this microplate reader 1, so that microplate reader 1 can be used in the measurement of microaerophilic or facultative anaerobic microorganisms under a defined $O_2$ concentration. The measurement of anaerobic microorganisms or eukaryotic cells under a defined $O_2$ concentration is thus enabled.

The control unit 6 in combination with a $CO_2$ sensor allows controlling the carbon dioxide content of the gas atmosphere 7 surrounding the wells 3 containing the samples of microplate(s) 4 inserted in this microplate reader 1, so that this microplate reader 1 can be used in the measurement of living cell cultures under a defined $CO_2$ concentration.

In connection with the present invention, cell cultures, biological cell accumulations separated from such cell cultures or obtained otherwise, or individual cells will be designated as cells, with such cells comprising microorganisms and fungi and animal and plant eukaryotic cells.

Any combination of the elements of the microplate reader 1 and the control unit 6 in accordance with the invention as shown in FIGS. 1 to 4 shall belong to the scope of the present invention.

The 5% $CO_2$ regulation of eukaryotic tumor cells was tested with a microplate reader 1 of the first embodiment in accordance with the invention (cf. FIG. 1). GFP-transfected A431 cells were used for fluorescence determination. The abbreviation GFP designates the generally known "green fluorescent protein" with excitation maximum at a wavelength of 396 nm and 475 nm, and with an emission maximum at a wavelength of 508 nm. In order to record the respective growth curves over 72 hours, these cells were suspended in media with 10% serum (MWS) or in media without serum (MWOS).

The medium with serum (MWS) had the following composition: Dulbecco's modified Eagle's Medium (DMEM containing phenol red) with 4.5 g/l glucose, supplemented by 10 mM of HEPES buffer, 2 mM of L-glutamine, 1 mM of Na-pyruvate, 100 U/ml of penicillin, 0.1 mg/ml of streptomycin and 5% (v/v) of fetal bovine serum (FBS). All media components were obtained from PAA laboratories, Linz, Austria.

The medium without serum (MWOS) contained the same components, but no fetal bovine serum (FBS).

Figure 5:
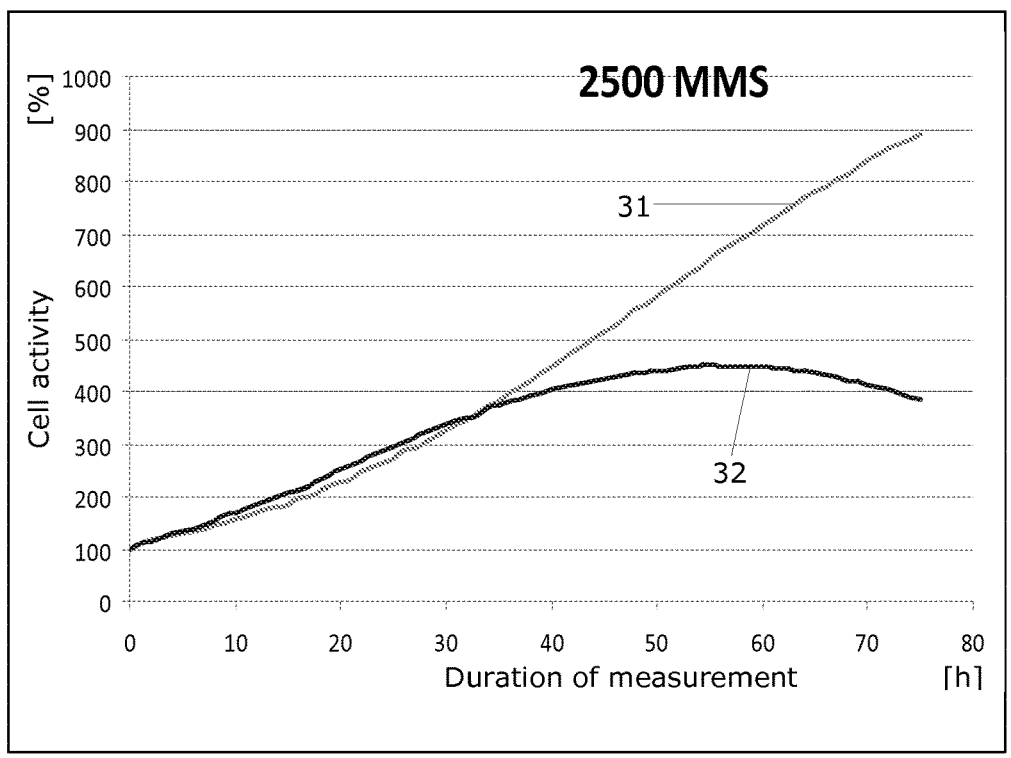
FIG. 5 shows growth curves of eukaryotic tumor cells in a medium with serum (MWS) by using a microplate reader in accordance with the invention with or without $CO_2$ control.

Microplates 4 of type Greiner Standard Cell Culture MTP 96 Well sterile coating (Greiner 96 well, black, flat & clear bottom, sterile-culture tissue plates) were used. 48 wells 3 of these microplates 4 were respectively charged with 2500 A431GFP cells and with 10% serum (sample type A, cf. FIG. 5). The remaining 48 wells of these microplates 4 were respectively charged with 2500 A431GFP cells without serum (sample type B, cf. FIG. 6). Two test series were performed with these 2 sample types A and B:

The first test series consisted of measuring the $CO_2$ concentration in the sample compartment 19 with a $CO_2$ sensor (SenseAir®, Typ $CO_2$ Engine® ICB, Part No.: 033-9-0001), which concentration was kept constantly at 5% with a control unit 6 with an integrated electronic control system. This was achieved in such a way that the atmosphere in the sample compartment 19 and in the appliance compartment 18 of the microplate reader 1 in accordance with the invention initially had a gas composition which corresponded to the one of the ambient air, i.e. it corresponded approximately to the standard atmosphere, which has the following composition: oxygen 20.93%, nitrogen 78.10%, argon 0.93%, carbon dioxide 0.03%, hydrogen, neon, helium, krypton and xenon 0.01%. The housing 17 of the microplate reader 1 was closed after the positioning of the microplate 4 on the holding device 5 of the microplate reader 1 and $CO_2$ gas was introduced into the sample compartment 19 via the gas inlet 21 until the $CO_2$ gas concentration reached 5%. This $CO_2$ concentration was held permanently over the duration of the measurement in that $CO_2$ gas was introduced into the sample compartment 19 as required (once the $CO_2$ sensor determined an inadequate carbon dioxide concentration). The gas mixture in the sample compartment 19 was circulated constantly with the fan 22. The temperature was kept constant at 37° C. in any case.

A second test series consisted of not introducing any additional $CO_2$ into the sample compartment 19 and thereby subjecting the samples permanently to ambient air. The temperature was kept constant at 37° in any case.

The fluorescence of each sample (each well 3) was respectively excited with a first illumination device 11' which was arranged beneath the microplate 4 (excitation at λ=485 nm; detection of fluorescence at λ=535 nm) and guided by means of the second optical system 23" to a photo multiplier tube 24 for detection. The individual fluorescence of the individual samples was measured depending on the time. The individual intensities of the fluorescence of every single well detected by the photo multiplier tube 24 were processed in the central computer 29 of the microplate reader 1 and then shown in curve diagrams (cf. FIGS. 5 and 6).

FIG. 5 shows growth curves of eukaryotic tumor cells in a medium with 10% serum (MWS) produced with or without $CO_2$ control by using a microplate reader 1 in accordance with the invention. The reference numeral 31 designates the samples in which the $CO_2$ concentration was kept permanently at 5%, and reference numerals 32 designates the samples which were subjected to normal ambient air. FIG. 5 shows that the cells acted approximately similarly during the first 35 hours, with cell vitality (measured on the basis of the corresponding GFP-signal (i.e. on the basis of intensity of fluorescence)) of the samples 31 in which the $CO_2$ concentration was kept permanently at 5% being permanently slightly lower than the cell vitality of the samples 32 which were subjected to normal ambient air. After approximately 35 hours, growth of the cells of the samples 32 which were subjected to normal ambient air slowed down dramatically. It reached a maximum of approximately 450% after approximately 60 hours and decreased thereafter to beneath 400% of the initial value at the end of the measurement at 75 hours. In contrast thereto, the cell vitality of the samples 31 in which the $CO_2$ concentration was kept permanently at 5% increased virtually linearly after 35 hours of measurement duration and reached approximately 900% of the initial value up until the end of the measurement at 75 hours.

Figure 6:
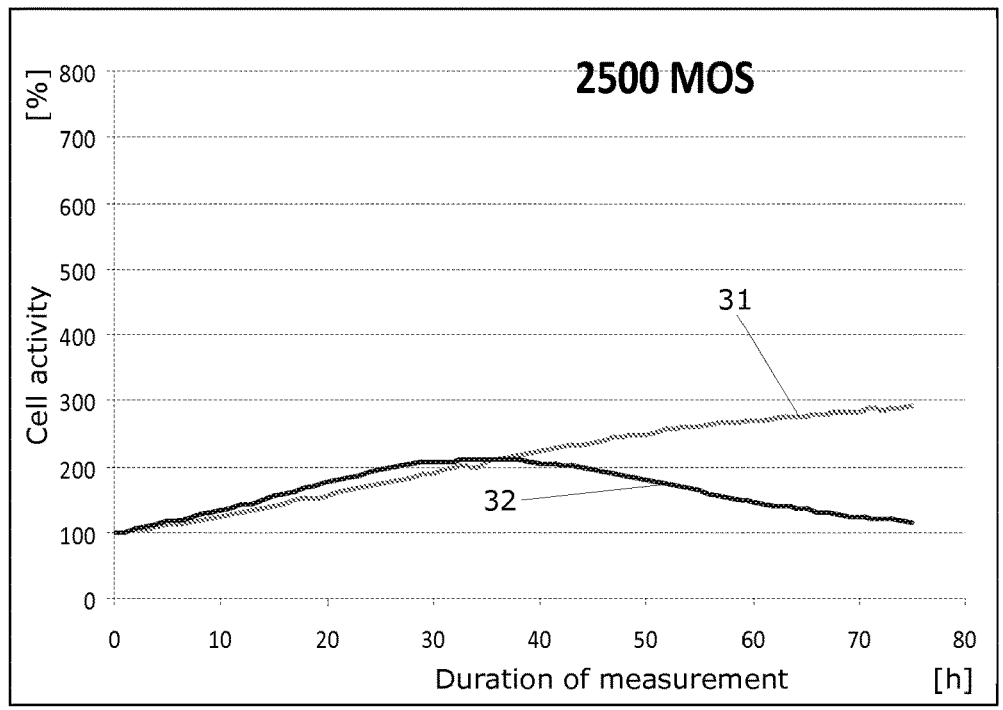
FIG. 6 shows growth curves of eukaryotic tumor cells in a medium without serum (MWOS) by using a microplate reader in accordance with the invention with or without $CO_2$ control.

FIG. 6 shows growth curves of eukaryotic tumor cells in a medium without 10% serum (MWOS) produced with or without $CO_2$ control by using a microplate reader 1 in accordance with the invention. The reference numeral 31 designates the samples in which the $CO_2$ concentration was kept permanently at 5%, and reference numerals 32 designates the samples which were subjected to normal ambient air. FIG. 6 shows that the cells acted approximately similarly during the first 35 hours, with cell vitality (measured on the basis of the corresponding GFP-signal (i.e. on the basis of intensity of fluorescence)) of the samples 31 in which the $CO_2$ concentration was kept permanently at 5% being permanently slightly lower than the cell vitality of the samples 32 which were subjected to normal ambient air. After approximately 35 hours, growth of the cells of the samples 32 which were subjected to normal ambient air reached a maximum of 200% and dropped to approximately the initial value of 100% up until the end of the measurement at 75 hours. In contrast thereto, the cell vitality of the samples 31 in which the $CO_2$ concentration was kept permanently at 5% increased in virtually the same amount even after approximately 35 hours of measurement duration and reached approximately 300% of the initial value up until the end of the measurement at 75 hours.

The illustrated results show that the cells held permanently under a $CO_2$ concentration of 5% are able to show substantially higher cell vitality than cells held under normal ambient air. This larger cell vitality plays a role especially after an incubation period of more than 40 hours. The further addition of 10% serum increases cell vitality during the first 35 hours approximately by a factor of 2, and even by a factor of 3 after 75 hours.

Such uninterruptible long-term studies actually become possible with the current invention, unlike conventional $CO_2$ incubators without integrated fluorescent measurement where typically a night window of approximately 14 hours during which no data can be collected needs to be taken into account.

No microplate readers are known from the state of the art which, comprise sensors and a control unit for controlling the composition of the gas atmosphere above the wells or in the ambient environment of the wells containing the samples of a microplate used in this microplate reader.

Although the German published application DE 10 2005 033 927 A1 discloses an illumination device for transmitted light contrast in the bright field for inverse microscopes for observing living cells, this illumination device is integrated in a hermetically sealed, light-proof and compact incubator of the inverse microscopes in such a way that each individual well of a sample holder arranged as a microtiter plate is illuminated successively and that simultaneously thermal stabilization of the sample volume is ensured over a prolonged period of time in combination with the lowest possible heat losses. This illumination device is arranged in a stationary manner in an upper part of the incubator and above a projection lens. An inserted microtiter plate, Petri dish or the like can be moved relative to the projection lens on a microscope stage arranged in a bottom part of the incubator. The incubator comprises a first in a chamber which is enclosed completely by an outer second chamber and is thereby thermally decoupled from the ambient environment. The microtiter plate with the samples is disposed in said inner chamber in which the temperature, the air humidity and the $CO_2$ content are controllable in a controlled manner by control devices. This German published application DE 10 2005 033 927 A1 relates exclusively to inverse microscopes, the configuration and use of which differ considerably from a microplate reader which does not comprise any imaging function and enables substantially shorter measuring periods per well. Microplate readers and especially $O_2$ sensors are not mentioned in this publication.

A climatic chamber for observing samples in microtiter plates is also known from the patent EP 1 575 706 B1. A conditioning stream of medium in the form of air with a defined air humidity and/or temperature can be introduced into this climatic chamber. The defined introduction of $CO_2$ gas and the arrangement of a temperature sensor, humidity sensor and/or gas sensor close to the sample holder carrying the microtiter plate can be provided. Microplate reader and especially $O_2$ sensors are not mentioned in this publication.

As a result, the state of the art does not make obvious to the person skilled in the art the microplate reader 1 in accordance with the invention with the control unit 6 for controlling the composition of a gas atmosphere 7 above or in the ambient environment of the wells 3 containing the samples of microplates 4 used in this microplate reader 1.

Further preferred applications of the microplate reader 1 and the control unit 6 in accordance with the invention relate for example to examinations with respect to the influence of $O_2$ partial pressure on the growth of microorganisms such as *Rhodospirillum rubrum* [Biedermann et al. 1967, "Archiv für Mikrobiologie" (Archive for Microbiology) 56, 133-147] and examinations on microaerophilic alginate production, in which preferably an $O_2$ concentration of 2.5-5% (preferably 2.5%) is to be set [Wael Sabra 1999: Microaerophilic alginate production with *Azotobacter vinelandii*; Dissertation at the Common Scientific Faculty of the Braunschweig University of Technology].

In the following, preferred embodiments of the microplate reader 1 are described, which are particularly adapted to control the temperature of the gas atmosphere 7 in the sample compartment 19. Such preferred embodiments are described with the help of the FIGS. 7 and 8. Though these preferred embodiments are here shown and described on the basis of a microplate reader as also described for FIG. 1, those features and their embodiments described for the microplate reader 1 as discussed for the other figures may also be applied or combined to embodiments of the microplate reader discussed below, even though they are not mentioned explicitly.

FIG. 7 shows in a highly schematic sectional view through a microplate reader 1 which is particularly suitable for providing a gas atmosphere 7 with a controlled temperature. In such a microplate reader 1 the control unit 6 comprises a cooling device 48 for cooling the gas atmosphere 7 in the sample compartment 19. In addition or as an alternative, the control unit 6 comprises a heating device 46 for heating the gas atmosphere 7 in the sample compartment 19. In FIG. 7 as well as in FIG. 8, a microplate reader 1 is shown comprising both, a cooling device 48 and a heating device 46, though it is possible that only a cooling device 48 or only a heating device 46 are present in a microplate reader 1.

In case when the microplate reader 1 comprises both, the cooling device 48 and the heating device 46, the temperature of the gas atmosphere 7 in the sample compartment 19 may be controlled in a very precise manner by a coordinated operation of these devices. E.g. a condensation of humidity respectively water on a microplate 4 inserted into the microplate reader 1 may be counteracted already by the coordination of the activity of the heating device 46 and/or the cooling device 48. The cooling device 46 enables a precise control of the sample compartment temperature near or below room temperature. By using both, a cooling device 48 and a heating device 46, the sample compartment temperature can be maintained precisely for prolonged periods, even if the room temperature has strong fluctuations.

However, a heating device 46 might not be necessary, for example in regions where the natural room temperature is relatively high. In this case, a basically higher temperature is present also in the interior space 16 of the microplate reader 1 simply due to the higher surrounding temperature and the temperature of the devices in the appliance compartment 18. In these cases it is sufficient to regulate the temperature of the sample compartment by the use of a cooling device 48 only, and without a counteracting heating device 46. Nevertheless, a more precise temperature regulation may be achieved by a combination of a heating device 46 and a cooling device 48.

In a preferred embodiment, the cooling device 48 is mounted on the bottom of the sample compartment 19 and is in heat exchange communication with the gas atmosphere 7 in said sample compartment 19. A heat exchange communication is preferred to ensure that the gas in the direct adjacencies of an activated cooling device 48 can be moved towards the holding device 5, so that samples in wells 3 of a microplate 4 which is inserted into the microplate reader 1, thus, which is accommodated and hold by the holding device 5, are surrounded by the cooled gas. Thus, the heat exchange communication ensures a gas exchange within the gas atmosphere 7 of the sample compartment 19, so that preferably a homogeneous temperature is achieved within the sample compartment 19.

Preferably in all embodiments, the microplate reader 1 comprises a support element 45 which is arranged within the sample compartment 19 and below the holding device 5. This support element 45 organizes the sample compartment 19 into a sample area 50 which comprises the holding device 5 and a cooling area 51 which comprises the cooling device 48. The support element 45 may be a plate which extends essentially parallel to the bottom of the sample compartment 19 and to the bottom of the microplate reader 1, as it is shown in FIG. 7. However, the support element 45 may be configured more complex as it is shown in FIG. 8.

To ensure that the air within the sample compartment 19 can be moved to achieve a homogeneous temperature distribution within the sample compartment 19 if e.g. the cooling device 48 is activated, the support element 45 is configured to provide the heat exchange communication between the sample area 50 and the cooling area 51 with respect to the gas atmosphere 7 in the sample compartment 19.

For this, the support element 45 preferably comprises ventilation openings 49. Air which is cooled in the direct vicinity of the cooling device 48 may be moved through these ventilation openings 49 from the cooling area 51 into the sample area 50. Such a circulation of air or gas, respectively, ensures that temperature of the gas atmosphere 7 in the sample compartment 19 is homogenously distributed when the cooling device 48 is activated.

In the FIGS. 7 and 8, different exemplary embodiments of such a support element 45 are shown. In FIG. 7, a support element 45 is shown which is essentially a plate mounted e.g. by support posts (not shown) on the bottom of the sample compartment 19. In case the separating plate 15 is configured as an interior housing 39, the support element 45 might be mounted on the bottom of said interior housing 39. Furthermore, the support element 45 shown in FIG. 7 comprises ventilation openings 49. In this sectional view, three openings 49 are shown, into all of which in each case a fan 52, 53 is mounted by example.

In FIG. 8, a more complex support element 45 is shown, with five ventilation openings 49 hit by the section. The support element 45 is not only a simple plate as shown in FIG. 7, but further comprises box-like extension structures above the central delivering fan 52. These structures accommodate at least partly devices e.g. for the so called bottom reading for the detection of fluorescence emitted by samples. This more complex configuration of the support element 45 might be desired for providing a protection against cooled air when the delivering fan 52 is positioned below temperature sensible devices and the cooling device 48 is activated. Additional ventilation openings 49 are provided in this box-like extension structure towards the sample area 50, thereby ensuring not only the heat exchange communication but also providing a direction for the movement of the air into the sample area 50. Alternatively, or in addition, guiding elements may be used together with the ventilation openings 49 for guiding moved air into a desired direction. In FIG. 7, such guiding elements are shown for those ventilation openings 49 which are arranged laterally.

The box-like structures in FIG. 8 are shown as being extensional structures of the support element 45. Alternatively, they may be configured as separate structures connected to a support plate 45. It is within the knowledge of a skilled person to configure a support element 45 which should provide on the one hand protection of temperature sensible devices against moved cooled air, to ensure the heat exchange communication and/or define a direction for the air moved by a delivering fan 52 towards the sample area 50. By way of example, the size, number, and positioning of ventilation openings 49, use of guiding structures, and use of distinctively directed fans in connection with a support plate 45 according to the present invention are suitable elements for addressing these requirements.

In FIG. 8, it is exemplarily shown that the support element 45 is on the right side mounted within the sample compartment 19 by the help of elongation structures which are configured to engage the inner side of a side wall of the housing 17 of the microplate reader 1. On the left end of the support element 45, such elongation structures are not shown, to indicate that other mounting systems may be used. Generally, it is within the knowledge of a skilled person how to mount a support element 45 described above within the microplate reader 1.

In a preferred embodiment, the cooling device 48 comprises a heat exchange device 40 which is connected via lines 44 to an external chiller 47. The heat exchange device 40 is adapted for cooling the gas atmosphere 7 in the sample compartment 19. The external chiller 47 is adapted for cooling the heat exchange device 40 by using a cooling medium which is cooled by the external chiller 47 and transported to the heat exchange device 40 by the lines 44.

The heat exchange device 40 and the lines 44 are preferably arranged within the cooling area, as shown in the FIGS. 7 and 8. The chiller 47 provides the heat exchange device 40 with a cooling medium for cooling the gas atmosphere in the adjacencies of the heat exchange device 40. The cooling medium might be a gas, a liquid, a solid or a mixture of these. A particularly suitable cooling medium is for example a mixture of water with an antifreeze agents. A preferred antifreeze agent is propylene glykol (1,2-Propanediol), which is miscible with water in any ratio and is inflammable, non-hazardous and non-irritating to skin.

Alternatively, the cooling medium may be cooled water which is provided by an external cooling water circuit. This might be preferred in cases where the microplate reader 1 is used e.g. in laboratories which are equipped with such an in-house cooling water system.

For bringing the cooling medium from the external chiller 47 to the heat exchange device 40 in the cooling area 51 of the sample compartment 19, the lines 44 are guided through the housing 17 of the microplate reader 1 by a corresponding cooling medium inlet 42, which is arranged for example in the rear wall 30 of the microplate reader 1. The lines 44 might be isolated in order to reduce energy consumption. After having passed the heat exchange device 40, the cooling medium might be reverted outwards via lines 44 and a corresponding cooling medium outlet 43 back to the external chiller 47, thereby closing the cooling circuit of the cooling medium.

Generally, the principle of a heat exchange device 40 for cooling surrounding air is known. To summarize: The heat exchange device 40 consists of a lamellar structure, which is cooled by the cooling medium when it passes internally through the heat exchange device 40. The surrounding air is forced through the lamellar structure by using an attached fan and thereby cools the air inside the heat exchange device 40. If the cooling medium is for example a cooling liquid, a liquid-air heat exchanger is used. As the heat exchange device 40 is positioned in the cooling area 51 of the sample compartment 19, and is in heat exchange communication with the gas atmosphere 7 of the sample area 50 of the sample compartment 19, the cooled air in the heat exchange device 40 may be moved within the sample compartment 19 until the complete gas atmosphere 7 has a homogeneous temperature.

Alternatively, a Peltier-Element or other cooling devices might be used as the element which cools the gas atmosphere 7 in the sample compartment 19, instead of a heat exchange device 40, as long as a heat exchange communication with the gas atmosphere 7 of the sample compartment 19 is ensured.

Preferably in all embodiments, the microplate reader 1 comprises a delivering fan 52 for moving the cooled gas from the heat exchange device 40 in the cooling area 51 towards the holding device 5 in the sample area 50 when it is required, e.g. during an incubation or a measurement of a sample contained in wells 3 of a microplate 4. In addition, or as an alternative, the microplate reader 1 comprises at least one purging fan 53 for moving gas from the holding device 5 towards the bottom of the sample compartment 19.

In FIG. 7, two purging fans 53 are shown in addition to a delivering fan 52; however, it might be suitable to use only one or more than two, e.g. four or even eight fans. In FIG. 8, a microplate reader 1 with only one delivering fan 52 and no purging fan 53 is shown. The preferred direction of moving air is indicated in the FIGS. 7 and 8 for each of the delivering fan 52 and the purging fans 53 by an arrow.

The fans 52, 53 shown in the FIGS. 7 and 8 serve to support the heat exchange, or the gas exchange, respectively, between the cooling area 51 and the sample area 50, and are preferably activated when the cooling device 48 is activated. One of these fans is arranged more centrally and serves as a delivering fan 52 which delivers cooled air from the cooling area 51 into the sample area 50. The other two fans shown in FIG. 7 serve as purging fans 53 which direct air from the sample area 50 to the cooling area 51 and thereby further support an optimal air circulation.

The delivering fan 52 shown in FIG. 7 is mounted in a central ventilation openings 49 for supporting the circulation of the gas for the heat exchange between the cooling area 51 and the sample area 50. In FIG. 8, a central ventilation opening 49 carrying the delivering fan 52 is shown, while the other ventilation openings 49 are shown as simple through holes in the support element 45 without fans. No purging fans 53 are for example required when the delivering fan 52 is strong enough to ensure an amount of air circulation which provides in a satisfactory time a homogenous temperature distribution within the sample compartment 19 when the cooling device 48 is activated.

Preferably in all embodiments, the microplate reader 1 comprises at least a delivering fan 52 for moving gas from the gas atmosphere 7 cooled by the heat exchange device 40 in the cooling area towards the holding device 5 and into the sample area 50. Preferably in all embodiments, the delivering fan 52 is mounted in a ventilation opening 49 of the support element.

For better controlling the humidity of the gas atmosphere 7 in the sample compartment 19, and to prevent condensation anywhere in the sample compartment 19 as much as possible, the microplate reader 1 preferably comprises a dehumidifier 41. By such a dehumidifier 41, excess humidity in the gas atmosphere 7 of the sample compartment 19 may be removed in a controlled manner. Preferably, the dehumidifier 41 is mounted in the cooling area 51 of the sample compartment 19, for example on the bottom of the sample compartment 19. Excess humidity in the gas atmosphere 7 will deposit on said dehumidifier 41 in the cooling area 51.

In the FIGS. 7 and 8, a dehumidifier is shown which is coupled to the cooling circuit of the heat exchange device 40. According to these embodiments, the cooling medium first passes from the external chiller 47 through the dehumidifier 41, is afterwards guided through the heat exchange device 40 and then transported back to the external chiller 47. For improving the cooling capacity, an additional Peltier element might be used for further cooling down the dehumidifier 41. In this case, the cooling medium is coupled to the Peltier-Element instead of being directly coupled to the dehumidifier 41 (not shown).

The control unit 6 of the microplate reader 1 might preferably comprise a heating device 46 for heating the sample compartment 19. The heating device 46 might be mounted on the zoning means 15, 39 or alternatively on the support element 45, and is in heat exchange communication with the gas atmosphere in the sample compartment. Most preferably, the heating device 46 is mounted on a surface of the zoning means 15, 39 or of the support element 45 which faces towards the sample compartment 19. In a preferred embodiment, the heating device 46 is a thin heating plate. The choice of suitable heating devices 46 for a microplate reader 1 is within the knowledge of a skilled person and is therefore not discussed in more detail here.

For measuring the temperature of the gas atmosphere 7 in the sample compartment 19 the control unit 6 preferably comprises in the sample compartment 19 a temperature sensor. The use of a temperature sensor allows a precise control of the temperature of the gas atmosphere 7 in the sample compartment 19, as the temperature may be monitored automatically, and e.g. in cases when the temperature of the gas atmosphere 7 in the sample compartment 19 exceeds a predefined threshold temperature, the cooling device 48 may be activated. In embodiments of the microplate reader 1 comprising a heating device 46, on the other hand, this heating device 46 may be activated when the temperature of the gas atmosphere 7 in the sample compartment 19 falls below a predefined threshold temperature. This provides an active regulation of the temperature, and allows a fast and precise adjustment of the temperature where necessary, e.g. when a microplate 4 with temperature sensitive samples is inserted into the microplate reader 1.

Preferably in addition, or as an alternative, the control unit 6 may comprise a humidity sensor for measuring the humidity of the gas atmosphere 7 in the sample compartment 19. This allows a precise control and adjustment of the humidity of the gas atmosphere 7 in the sample compartment 19 e.g. supplementary to the control and regulation of the temperature of the gas atmosphere 7.

For controlling the temperature of the gas atmosphere 7 in the sample compartment 19, it may be provided that the cooling device and the heating device 46 are actuated separately. Preferably, the regulation of the actuation of the cooling device 48 and the heating device 46 is under a common control provided by the control unit 6.

The temperature control of the gas atmosphere 7 in the sample compartment 19 as described above preferably is provided in addition to the control of the composition of the gas atmosphere 7 in the sample compartment 19. However, it might be desirable to equip the microplate reader with the temperature control of the gas atmosphere 7 in the sample compartment 19, but with the control for the respective gas composition 7 as only an optional feature.

Same or corresponding features of the microplate-reader 1 shown in the Figures are provided with same reference numerals, also when this is not expressly referred to in the description. Also, arbitrary combinations of features of embodiments shown the Figures resp. of technical equivalents of these features belong to the scope of the invention as herein disclosed.

| List of reference numerals: | |
| --- | --- |
| 1 | Microplate reader |
| 2' | First measuring device |
| 2" | Second measuring device |
| 2''' | Third measuring device |
| 3 | Wells |
| 4 | Microplate |
| 5 | Holding device |
| 6 | Control unit |

| List of reference numerals: | |
|---|---|
| 6' | Separate control unit |
| 7 | Gas atmosphere |
| 8 | O₂ sensor |
| 9 | CO₂ sensor |
| 10 | Injector apparatus |
| 11' | First illumination device |
| 11" | Second illumination device |
| 12 | First side of an inserted microplate |
| 13' | First optical axis |
| 13" | Second optical axis |
| 13''' | Third optical axis |
| 14 | Second side of an inserted microplate |
| 15 | Separating plate |
| 16 | Interior space |
| 17 | Housing of the reader |
| 17' | Separate housing |
| 18 | Appliance compartment |
| 19 | Sample compartment |
| 20 | Opening |
| 21 | Gas inlet |
| 22 | Fan |
| 23' | First optical system |
| 23" | Second optical system |
| 23''' | Third optical system |
| 24 | PMT photo multiplier tube |
| 25 | Mirror |
| 26 | Partially transparent mirror |
| 27 | Electrical contacts |
| 28 | Computer |
| 29 | Central computer of 1 |
| 30 | Rear wall |
| 31 | Growth curve of cells with CO₂ control |
| 32 | Growth curve of cells without CO₂ control |
| 33' | First fiber-optical line |
| 33" | Second fiber-optical line |
| 33''' | Third fiber-optical line |
| 34' | First fiber slide |
| 34" | Second fiber slide |
| 35' | First monochromator |
| 35" | Second monochromator |
| 36 | Flash lamp |
| 37' | First filter |
| 37" | Second filter |
| 38 | Gas lines |
| 39 | interior housing |
| 40 | heat exchange device |
| 41 | Dehumidifier |
| 42 | Cooling medium inlet |
| 43 | Cooling medium outlet |
| 44 | Lines |
| 45 | Support element |
| 46 | Heating device |
| 47 | External chiller |
| 48 | Cooling device |
| 49 | Ventilation opening |
| 50 | Sample area |
| 51 | Cooling area |
| 52 | Delivering fan |
| 53 | Purging Fan |

What is claimed is:

1. A microplate reader, comprising:
a) a housing surrounding an interior space of the microplate reader, the interior space having a top wall and a bottom wall which oppose each other with connected side walls disposed therebetween:
b) a zoning means extending between the side walls of the interior space and subdividing the interior space of the housing into an appliance compartment and a sample compartment, with the appliance compartment positioned above the sample compartment,
wherein the zoning means provides substantially gas-tight separation between the appliance compartment and the sample compartment; wherein the appliance compartment is bound by the top wall, the zoning means, and the side walls; wherein the sample compartment is bound by the bottom wall, the zoning means, and the side walls; wherein the sample compartment contains a holding device adapted to hold a microplate having samples in wells, and is configured to hold a gas atmosphere which contacts said samples in wells when said microplate is provided in the microplate reader,
said zoning means being fixed within the housing of the microplate reader, and comprising at least one opening configured such that light emitted by samples in wells of said microplate accommodated in the holding device can pass through the opening from the sample compartment to the appliance compartment, said zoning means being a separating plate or an interior housing comprising at least one opening therein;
c) at least one measuring device arranged in the appliance compartment for measuring light received from samples in wells of said microplate accommodated in the holding device;
d) wherein the holding device is adapted to move microplates held therein, the holding device being movable with respect to the at least one measuring device, to the zoning means, and to the opening in the zoning means, along at least one axis of a Cartesian coordinate system;
wherein the holding device is surrounded by the gas atmosphere in the sample compartment during use; wherein the holding device is located and movable within a sample area of the sample compartment;
e) a control unit configured to control the temperature of the gas atmosphere in the sample compartment, the control unit being operatively connected to a cooling device, wherein the control unit is configured to actuate the cooling device for controlling temperature;
f) a first illumination device, a first fiber-optical line, and a first optical element, the illumination device comprising a flash lamp and a first wavelength-selective monochromator and being adapted for irradiating samples in the wells of said microplate accommodated in the holding device with light of a selected wave length, wherein the first fiber-optical line connects the first illumination device with the first optical element, and wherein the first optical element is adapted to guide light for irradiating samples against the samples in the wells of said microplate; wherein the first optical element is located in one of the at least one openings of the separating plate;
g) a support element mounted in the sample compartment, the support element comprising a plate positioned above and extending substantially parallel to said bottom wall of the interior space, the support element being positioned below both the zoning means and the holding device, wherein the support element separates the sample area of the sample compartment above the support element and a cooling area of the sample compartment below the support element at the bottom end of the interior space of the housing;
wherein said cooling device is positioned in the cooling area of the sample compartment for cooling the gas atmosphere in the sample compartment; and wherein the support element comprises a delivering fan arranged for moving air which has been cooled by the cooling device upwards from the cooling area below the support element to the sample area above the support element;

wherein the sample area of the sample compartment is located between the appliance compartment and the cooling area of the sample compartment; and wherein the holding device is separate from and is movable with respect to both the support element and the zoning means.

2. A microplate reader according to claim 1, wherein the support element comprises at least one ventilation opening for passage of gas atmosphere between the sample area and the cooling area.

3. A microplate reader according to claim 1, wherein the cooling device comprises a heat exchange device which is connected via lines to an external chiller, the heat exchange device being configured for cooling the gas atmosphere in the sample compartment, and the external chiller being configured for cooling the heat exchange device by a chiller medium which is cooled by the external chiller and transported to the heat exchange device by the lines.

4. A microplate reader according to claim 2, wherein the delivering fan is mounted in a ventilation opening of the support element.

5. A microplate reader according to claim 1, comprising a dehumidifier for condensing excess humidity in the gas atmosphere of the sample compartment.

6. A microplate reader according to claim 5, wherein the dehumidifier is mounted on the bottom wall and within the cooling area.

7. A microplate reader according to claim 1, further comprising a heating device for heating the sample compartment, wherein the heating device is in heat exchange communication with the gas atmosphere in the sample compartment.

8. A microplate reader according to claim 1, further comprising a heating device for heating the sample compartment, wherein the heating device is mounted on the support element and is in heat exchange communication with the gas atmosphere in the sample compartment.

9. A microplate reader according to claim 1, wherein the control unit comprises at least one of a temperature sensor for measuring a temperature of the gas atmosphere in the sample compartment and a humidity sensor for measuring a humidity of the gas atmosphere in the sample compartment.

10. A microplate reader according to claim 1, wherein the control unit is further configured to control the composition of the gas atmosphere in the sample compartment.

11. A method of cooling a gas atmosphere of a sample compartment in a microplate reader, the method comprising:
providing a microplate reader, the microplate reader comprising:
a) a housing surrounding an interior space, the interior space having a top wall and a bottom wall which oppose each other with connected side walls disposed therebetween;
b) a zoning means which divides the interior space of the housing into an appliance compartment and a sample compartment, the appliance compartment being above the sample compartment,
wherein the appliance compartment is defined by at least the top wall and the zoning means, and the sample compartment is defined by at least the bottom wall and the zoning means; wherein the sample compartment contains a microplate held in a holding device, and is provided with a gas atmosphere which contacts samples in wells of the microplate, said zoning means being fixed within the housing of the microplate reader and comprising at least one opening such that light emitted by said samples in wells of the microplate in the microplate reader passes through the opening from the sample compartment to the appliance compartment, said zoning means being a separating plate or an interior housing comprising at least one opening therein;
c) at least one measuring device arranged in the appliance compartment for measuring light received from samples in wells of the microplate;
d) wherein the holding device is configured to move microplates held therein, the holding device being movable with respect to the at least one measuring device, to the zoning means, and to the opening in the zoning means, along at least one axis of a Cartesian coordinate system; wherein the holding device is surrounded by the gas atmosphere in the sample compartment;
e) a control unit adapted to control the temperature of the gas atmosphere in the sample compartment, the control unit comprising a cooling device, wherein the control unit is configured to actuate the cooling device for controlling temperature;
f) a first illumination device, a first fiber-optical line, and a first optical element, the illumination device comprising a flash lamp and a first wavelength-selective monochromator and being adapted for irradiating samples in the wells of said microplate accommodated in the holding device with light of a selected wave length, wherein the first fiber-optical line connects the first illumination device with the first optical element, and wherein the first optical element is adapted to guide light for irradiating samples against the samples in the wells of said microplate; wherein the first optical element is located in one of the at least one openings of the separating plate;
g) a support element mounted in the sample compartment, the support element comprising a plate positioned above and extending substantially parallel to said bottom of the sample compartment, the support element being positioned below both the zoning means and the holding device, wherein a sample area of the sample compartment is above the support element and a cooling area of the sample compartment is below the support element; wherein said cooling device is positioned in the cooling area of the sample compartment for cooling the gas atmosphere in the sample compartment; and wherein the support element comprises a delivering fan arranged for moving air which has been cooled by the cooling device upwards from the cooling area to the sample area; the method further comprising the steps of:
providing a gas atmosphere in the sample compartment,
cooling the gas atmosphere with the cooling device, and
moving cooled gas atmosphere from the cooling area to the sample area using the delivering fan.

12. The method of claim 11, wherein the control unit comprises a temperature sensor for measuring a temperature of the gas atmosphere in the sample compartment, the method further comprising:
measuring the temperature of the gas atmosphere in the sample compartment with the temperature sensor; determining that the temperature of the gas atmosphere exceeds a threshold temperature; and activating the cooling device in response to said determination that the gas atmosphere exceeds the threshold temperature.

13. The method of claim 12, wherein the microplate reader comprises a heating device for heating the sample compartment, said heating device being in heat exchange communication with the gas atmosphere in the sample compartment, the method further comprising:

measuring the temperature of the gas atmosphere in the sample compartment with the temperature sensor; determining that the temperature of the gas atmosphere is less than a threshold temperature; and activating the heating device in response to said determination that the gas atmosphere exceeds the threshold temperature.

14. The method of claim 11, further comprising:

one of transilluminating and irradiating a first sample in a first well of the microplate with light of a selected wavelength; and measuring light from the sample using the at least one measuring device.

15. The method of claim 11:

wherein the support element comprises a horizontal plate, the horizontal plate being positioned between the cooling device below and the holding device and zoning means above;

wherein a plurality of ventilation openings through a thickness of the horizontal plate allow passage of gas atmosphere through the horizontal plate; and wherein at least one fan is provided in a ventilation opening of the horizontal plate, the at least one fan being oriented to blow gas atmosphere upwards; the method further comprising the step of using the at least one fan to blow cooled gas atmosphere upwards through the horizontal plate from the cooling area into the sample area.

16. The microplate reader according to claim 1:

wherein the support element comprises a horizontal plate, the horizontal plate being positioned between the cooling device below and the holding device and zoning means above;

wherein a plurality of ventilation openings through a thickness of the horizontal plate allow passage of gas atmosphere through the horizontal plate; and wherein at least one fan is provided in a ventilation opening of the horizontal plate, the at least one fan being oriented to blow gas atmosphere in a direction perpendicular to the horizontal plate.

* * * * *